(12) United States Patent
Yoshimura

(10) Patent No.: US 10,420,575 B2
(45) Date of Patent: Sep. 24, 2019

(54) TREATMENT TOOL AND TREATMENT TOOL SYSTEM

(71) Applicant: OLYMPUS CORPORATION, Tokyo (JP)

(72) Inventor: Katsuhiko Yoshimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 143 days.

(21) Appl. No.: 15/408,951

(22) Filed: Jan. 18, 2017

(65) Prior Publication Data

US 2017/0119418 A1 May 4, 2017

Related U.S. Application Data

(63) Continuation of application No. PCT/JP2015/066235, filed on Jun. 4, 2015.

(30) Foreign Application Priority Data

Jul. 25, 2014 (JP) ................................. 2014-151798

(51) Int. Cl.
*A61B 17/29* (2006.01)
*A61B 17/34* (2006.01)
(Continued)

(52) U.S. Cl.
CPC ................ *A61B 17/29* (2013.01); *A61B 1/00* (2013.01); *A61B 1/00149* (2013.01);
(Continued)

(58) Field of Classification Search
CPC ............ A61B 17/29; A61B 2017/2906; A61B 2017/2908; A61B 2017/2919;
(Continued)

(56) References Cited

U.S. PATENT DOCUMENTS

2008/0033240 A1 2/2008 Hoffman et al.
2009/0299136 A1* 12/2009 Hasegawa ............ A61B 1/0051
600/106
(Continued)

FOREIGN PATENT DOCUMENTS

EP 2123210 A1 11/2009
JP H06-105806 A 4/1994
(Continued)

OTHER PUBLICATIONS

Extended Supplementary European Search Report dated Dec. 12, 2017 in European Patent Application No. 15 82 5510.9.
(Continued)

*Primary Examiner* — Shaun L David
*Assistant Examiner* — Brigid K Byrd
(74) *Attorney, Agent, or Firm* — Scully, Scott, Murphy & Presser, P.C.

(57) ABSTRACT

A treatment tool includes: a support portion which is formed in an axial shape; a treatment portion which is disposed at a distal end portion of the support portion; a treatment assisting portion which is disposed at the distal end portion of the support portion, which has an assisting portion, and in which the assisting portion is capable of being moved between a first position and a second position; a driving portion which moves the assisting portion of the treatment assisting portion; an operation detection portion which determines an amount of movement of the support portion, which is inserted into an introducing tool, with respect to the introducing tool, and an orientation of the support portion; an operating portion which is disposed at a proximal end portion of the support portion; and a control portion which controls the driving portion based on a detection result of the operation detection portion.

13 Claims, 13 Drawing Sheets

(51) Int. Cl.
*A61B 1/00* (2006.01)
*A61B 34/00* (2016.01)
*A61B 17/28* (2006.01)

(52) U.S. Cl.
CPC .......... *A61B 17/28* (2013.01); *A61B 17/3423* (2013.01); *A61B 34/70* (2016.02); *A61B 2017/292* (2013.01); *A61B 2017/3447* (2013.01); *A61B 2562/0219* (2013.01)

(58) Field of Classification Search
CPC ..... A61B 2017/2938; A61B 2017/2901–2948; A61B 34/77; A61B 1/00039; A61B 1/00043; A61B 1/00137; A61B 1/00011; A61B 1/00006; B25J 9/1674; B25J 9/1689; B25J 9/06; B25J 9/0084; B25J 9/0087; B25J 9/009; B25J 9/0096; B25J 9/1669; B25J 9/1682; B25J 7/00; B25J 15/0019; B25J 15/0052; B25J 15/0253; G05B 19/418; G05B 19/41835; G05B 19/41865; G05B 2219/35472; G05B 2219/35247; G05B 2219/36445; G05B 2219/39445; G05B 2219/40399; G05B 2219/39209; G05B 2219/40191; G05B 2219/40402

USPC ........................................................ 606/205
See application file for complete search history.

(56) References Cited

U.S. PATENT DOCUMENTS

2011/0071347 A1    3/2011  Rogers et al.
2014/0277107 A1*   9/2014  Ishida ................... A61B 17/29
                                                   606/205

FOREIGN PATENT DOCUMENTS

| JP | H08-275958 A | 10/1996 |
| JP | 2004-135781 A | 5/2004 |
| JP | 2008-194302 A | 8/2008 |
| JP | 2009-512514 A | 3/2009 |
| JP | 2013-138717 A | 7/2013 |
| WO | WO 2007/047782 A2 | 4/2007 |
| WO | WO 2013/100171 A1 | 7/2013 |

OTHER PUBLICATIONS

International Search Report dated Jul. 28, 2015 issued in PCT/JP2015/066235.

* cited by examiner

TREATMENT TOOL AND TREATMENT TOOL SYSTEM

This application is a continuation application based on a PCT International Application No. PCT/JP2015/066235, filed on Jun. 4, 2015, whose priority is claimed on Japanese Patent Application No. 2014-151798, filed Jul. 25, 2014. The contents of both of the PCT International Application and the Japanese Patent Application are incorporated herein by reference.

BACKGROUND OF THE INVENTION

Field of the Invention

The present invention relates to a treatment tool by which treatment is performed via a hole formed in an abdominal wall and a treatment tool system including the treatment tool.

Description of Related Art

In the related art, in laparoscopic surgery using a laparoscope, treatment is performed by inserting a plurality of treatment tools or a laparoscope through a hole (an opening) that is open in an abdominal wall.

In "dissection" to divide an organ and an organ or a membrane which connects the organ and the organ to easily perform treatment, there is a need to perform the dissection using another treatment tool while grasping the organ or the membrane serving as a target using one or more treatment tools and applying an appropriate traction (a pulling force and tension), and a delicate operation in which a plurality of treatment tools are co-operated.

In particular, in the case of a large organ, there is a need to grasp/displace the organ using one treatment tool to secure an operative field and to perform dissection using another treatment tool while applying traction to a portion near a portion on which the dissection is performed using another treatment tool, and cooperation of these treatment tools becomes more important.

Generally, when the plurality of treatment tools are used as described above, an operation is performed while a surgeon cooperates with an assistant. However, as a system in which the plurality of treatment tools are independently operated by one surgeon, for example, a surgery manipulator device disclosed in Japanese Unexamined Patent Application, First Publication No. H8-275958 is proposed.

The surgery manipulator device of Japanese Unexamined Patent Application, First Publication No. H8-275958 has first and second observing slave manipulators and first to fourth treating slave manipulators that are attached to an attaching base provided at an edge of a bed on which a patient is placed.

The observing slave manipulators include a first shaft, a second shaft, and a third shaft which are driven by an electric motor and a fourth shaft and a fifth shaft which are configured by free joints. An endoscope is detachably fixed to a distal end holding portion that is disposed at the fifth shaft. An image captured by the endoscope is displayed on a display portion of a display device.

On the other hand, the treating slave manipulators are configured substantially similar to the observing slave manipulators. An electric treatment tool is detachably fixed to the distal end holding portion of one of the treating slave manipulators.

The surgery manipulator device has first and second treating master manipulators. Signals output from the first and second treating master manipulators are input to a corresponding control circuit. The control circuit sends control signals to the first to fourth treating slave manipulators via first and second switching circuits. Also, the first to fourth treating slave manipulators are operated to follow operations of the first and second treating master manipulators.

The first and second switching circuits are switched by operating a changeover switch.

The first and second treating slave manipulators which follow the first treating master manipulator can be selected by the first switching circuit. The third and fourth treating slave manipulators that follow the second treating master manipulator can be selected by the second switching circuit.

In the surgery manipulator device configured in this way, treatment is performed via a plurality of holes formed on an abdominal wall of the patient that correspond to the first to fourth treating slave manipulators.

As the first and second switching circuits are switched by the changeover switch, treatment can even be performed by only one surgeon by using the plurality of slave manipulators and switching the slave manipulators which are used.

SUMMARY OF THE INVENTION

According to a first aspect of the present invention, a treatment tool includes a support portion which is formed in an axial shape; a treatment portion which is disposed at a distal end portion of the support portion and by which treatment is performed; a treatment assisting portion which is disposed at the distal end portion of the support portion, which has an assisting portion configured to assist an operation of the treatment portion at a time of treatment, and in which the assisting portion is capable of being moved between a first position near the treatment portion and a second position moved from the first position in a direction which intersects a longitudinal axis of the support portion to be spaced apart from the treatment portion; a driving portion which moves the assisting portion of the treatment assisting portion; an operation detection portion which determines an amount of movement of the support portion, which is inserted into an introducing tool, with respect to the introducing tool, and an orientation of the support portion; an operating portion which is disposed at a proximal end of the support portion; and a control portion which controls the driving portion based on a detection result of the operation detection portion.

According to a second aspect of the present invention, in the treatment tool according to the first aspect, the treatment tool further includes: a movement instruction portion which determines an input by an operator and transmits a detection result to the control portion, wherein the control portion may have, as control mode, a first mode which controls the driving portion based on the detection result of the movement instruction portion; and a second mode which controls the driving portion based on the detection result of the operation detection portion, and wherein the treatment tool may be provided with a mode-switching portion configured to switch the control mode of the control portion between the first mode and the second mode.

According to a third aspect of the present invention, in the treatment tool according to the second aspect, in the second mode, the control portion may control the driving portion such that the distance between the treatment portion and the assisting portion of the treatment assisting portion is not a predetermined distance or less.

According to a fourth aspect of the present invention, in the treatment tool according to a third aspect, in the second mode, the control portion may control the driving portion such that a position of the assisting portion of the treatment assisting portion is not moved.

According to a fifth aspect of the present invention, in the treatment tool according to the third aspect, in the second mode, the control portion may control the driving portion such that the assisting portion of the treatment assisting portion is moved in a direction which is opposite to a direction in which the treatment portion is moved.

According to a sixth aspect of the present invention, in the treatment tool according to any one of the first to fifth aspects, the assisting portion of the treatment assisting portion may be capable of being moved in a first direction and a second direction which are perpendicular to each other with respect to a proximal end of the treatment assisting portion.

According to a seventh aspect of the present invention, in the treatment tool according to any one of the first to sixth aspects, the treatment assisting portion may have a plurality of joints which join ends of a plurality of links, and rotating axes about which the joints rotate the links may be parallel to each other.

According to an eighth aspect of the present invention, in the treatment tool according to the sixth aspect, the treatment tool further includes: the movement instruction portion which determines the input by the operator and transmits the detection result to the control portion, wherein the movement instruction portion may be provided at the operating portion and may be capable of being moved in a first indication direction and a second indication direction which are perpendicular to each other with respect to the operating portion, and the control portion may move the assisting portion of the treatment assisting portion in the first direction with respect to the proximal end of the treatment assisting portion based on the detection result transmitted from the movement instruction portion when the movement instruction portion is moved in the first indication direction with respect to the operating portion and move the assisting portion of the treatment assisting portion in the second direction with respect to the proximal end of the treatment assisting portion when the movement instruction portion is moved in the second indication direction with respect to the operating portion.

According to a ninth aspect of the present invention, in the treatment tool according to any one of the first to seventh aspects, the treatment tool further includes: the movement instruction portion which determines the input by the operator and transmits the detection result to the control portion, wherein the treatment assisting portion may have the plurality of joints which join the ends of the plurality of links, and the control portion may be configured to change an angle which is formed by adjacent links based on the detection result transmitted from the movement instruction portion.

According to a tenth aspect of the present invention, in the treatment tool according to any one of the first to ninth aspects, when the assisting portion of the treatment assisting portion is disposed at the first position, the assisting portion of the treatment assisting portion may be disposed closer to a distal end side than a distal end of the treatment portion.

According to an eleventh aspect of the present invention, in the treatment tool according to any one of the first to tenth aspects, the treatment tool further includes: a treatment operation portion which operates the treatment portion, wherein the treatment portion may be provided with a grasping portion having a pair of grasping pieces which are capable of being opened or closed, the assisting portion of the treatment assisting portion may have a pair of assisting-portion grasping pieces which are capable of being opened or closed, and the treatment operation portion may be configured to open or close the pair of grasping pieces of the grasping portion.

According to a twelfth aspect of the present invention, in the treatment tool according to any one of the first to eleventh aspects, the treatment assisting portion may be provided with a grasping rotary portion which rotates the assisting portion around an axis which is parallel to the longitudinal axis with respect to the distal end portion of the support portion.

According to a thirteenth aspect of the present invention, in the treatment tool according to the seventh aspect, the treatment assisting portion may be provided with a rotating portion which rotates a distal end side of a proximal end link around a longitudinal axis of the proximal end link which is disposed closest to a proximal end side of the plurality of links with respect to a proximal end side of the proximal end link.

A treatment tool system according to a fourteenth aspect of the present invention includes: the treatment tool according to the first aspect; and an introducing tool into which a support portion of the treatment tool is inserted.

DETAILED DESCRIPTION OF THE INVENTION (First Embodiment)

Hereinafter, a first embodiment of a treatment tool system according to the present invention will be described with reference to FIGS. 1 to 19.

Figure 1:
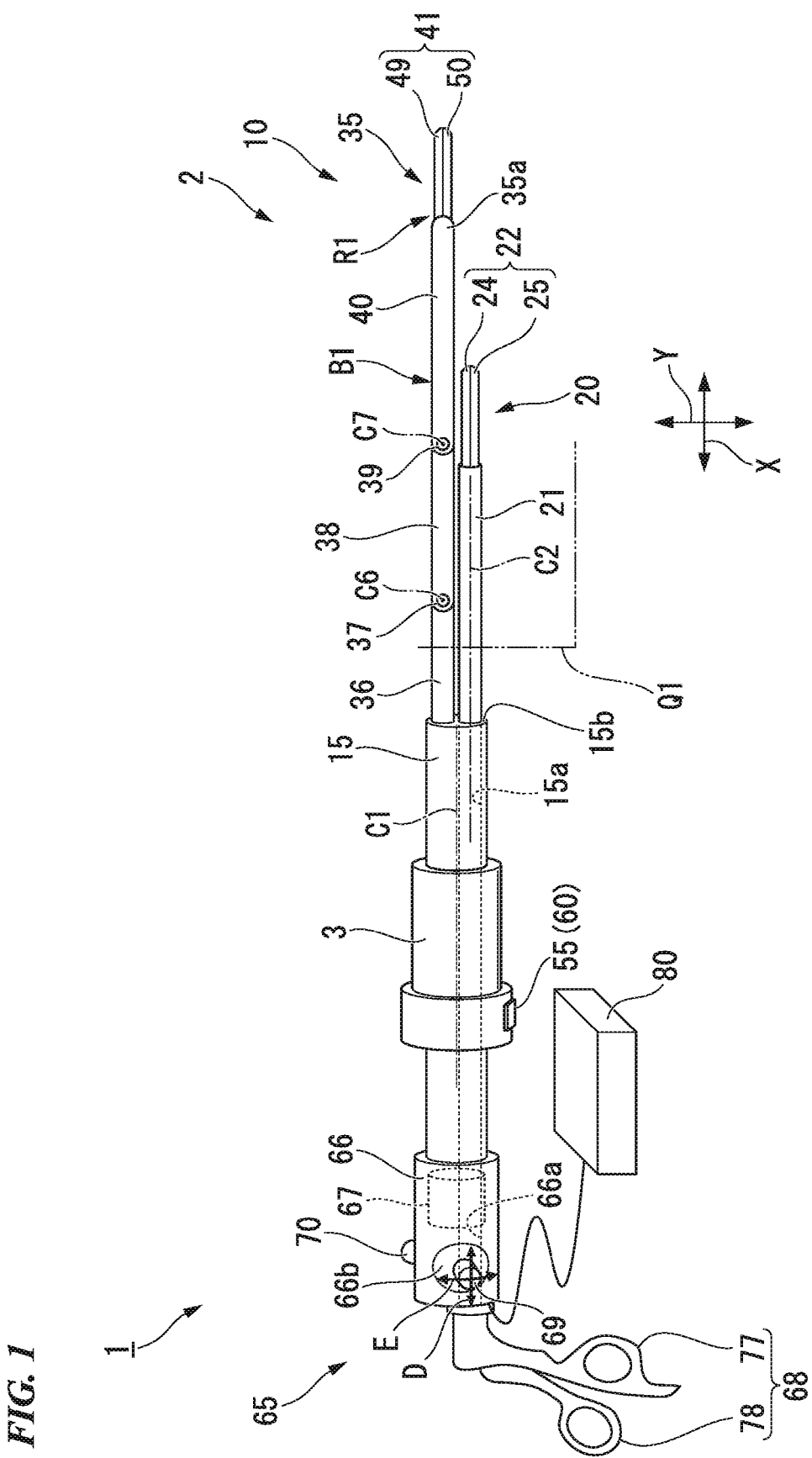
FIG. 1 is an overall diagram of a treatment tool system according to a first embodiment of the present invention.

As shown in FIG. 1, a treatment tool system 1 according to the present embodiment includes a treatment tool 2 according to the present embodiment and a trocar (an introducing tool) 3 into which an insertion portion 10 of the treatment tool 2 is inserted.

The trocar 3 is formed in a cylindrical shape and has a well-known configuration by which the trocar 3 is attached to a hole formed in an abdominal wall of a patient.

Figure 2:
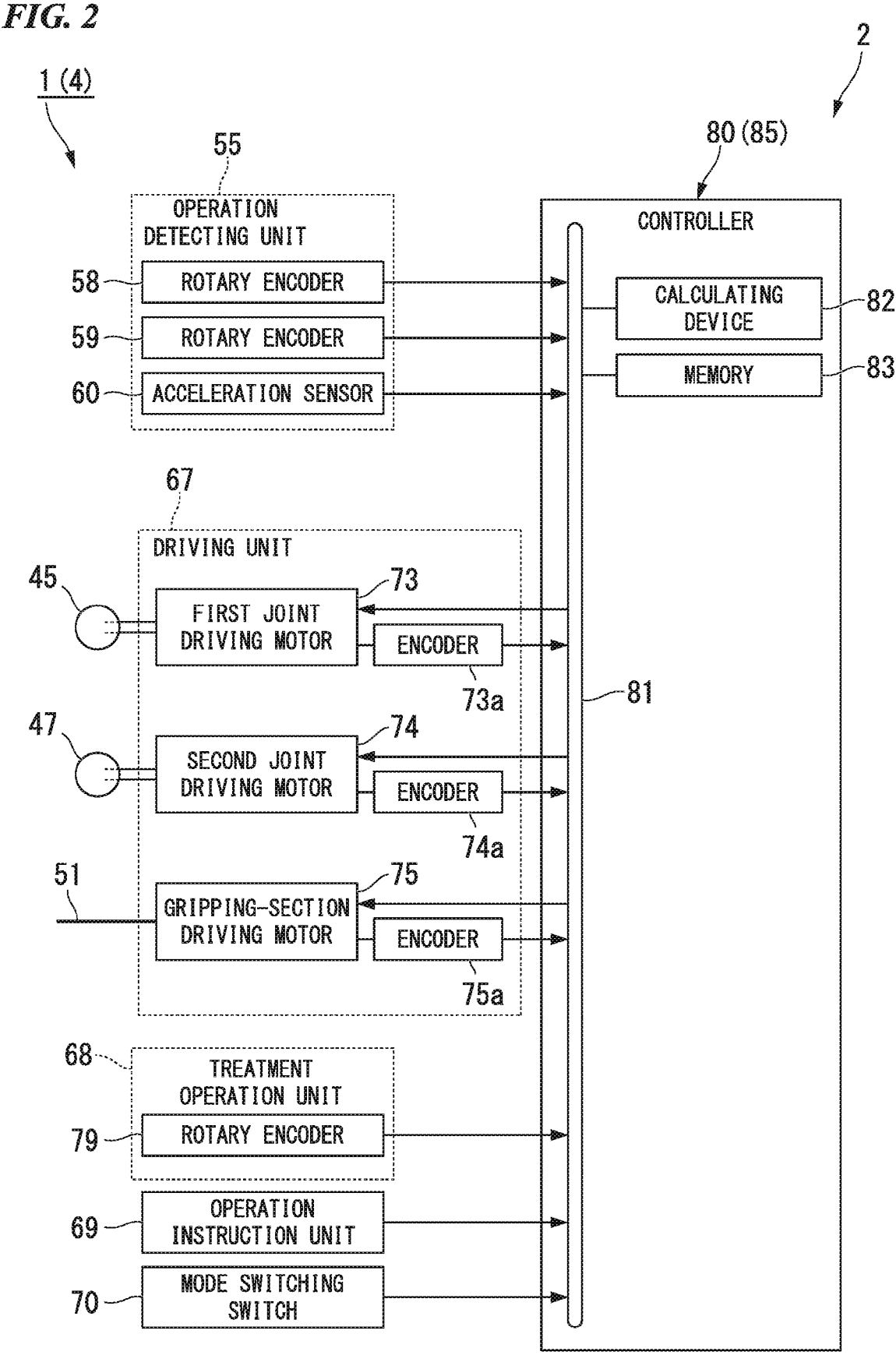
FIG. 2 is a block diagram of the treatment tool system according to the first embodiment of the present invention.

As shown in FIGS. 1 and 2, the treatment tool 2 has the elongated insertion portion 10 which can be insert into an abdominal cavity of the patient, an operation detection portion 55 which is attached to the trocar 3, an operation portion 65 which is disposed at a proximal end portion of the insertion portion 10, and a control portion 80 which controls the operation portion 65. Hereinafter, the insertion portion 10 side with respect to the operation portion 65 and the operation portion 65 side with respect to the insertion portion 10 are referred to as a distal end side and a proximal end side, respectively.

The insertion portion 10 has an outer cylindrical tube (a support portion) 15 that is formed in an axial shape and a treatment portion 20 and a treatment assisting portion 35 which are provided at a distal end portion of the outer cylindrical tube 15.

The outer cylindrical tube 15 is formed in a columnar shape using a metal with biocompatibility such as stainless steel and is rigid. An outer diameter of the outer cylindrical tube 15 is substantially the same as an inner diameter of the trocar 3.

Figure 3:
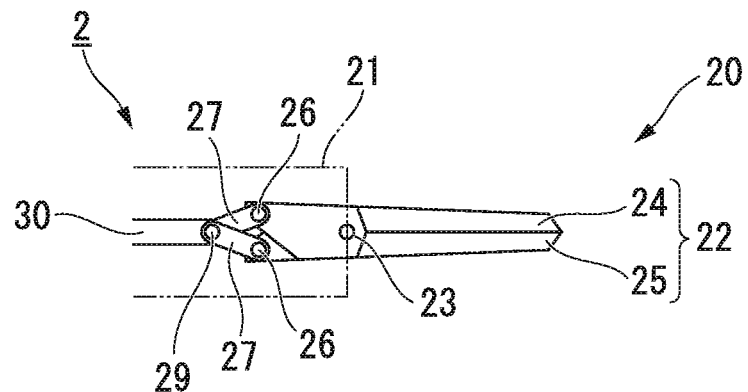
FIG. 3 is a side view showing a state in which a treatment portion of a treatment tool according to the first embodiment of the present invention is closed.

In the treatment portion 20, as shown in FIGS. 1 and 3, a distal end portion of a treatment insertion portion 21, which is formed in a cylindrical shape, has a grasping portion 22. Note that, in FIG. 3 and FIG. 4, which will be described below, a two-dot chain line is shown to transmit the treatment insertion portion 21 for the convenience of description.

The grasping portion 22 has a pair of grasping pieces 24 and 25 that are rotatably supported by a pin 23 at the distal end portion of the treatment insertion portion 21. Central portions of the grasping pieces 24 and 25 in longitudinal directions thereof are supported by the pin 23. Proximal end portions of the grasping pieces 24 and 25 are rotatably joined to one ends of intermediate links 27 via pins 26. The other ends of the intermediate links 27 are joined to a distal end portion of an operation rod (a power transmission portion) 30 via a pin 29.

Figure 4:
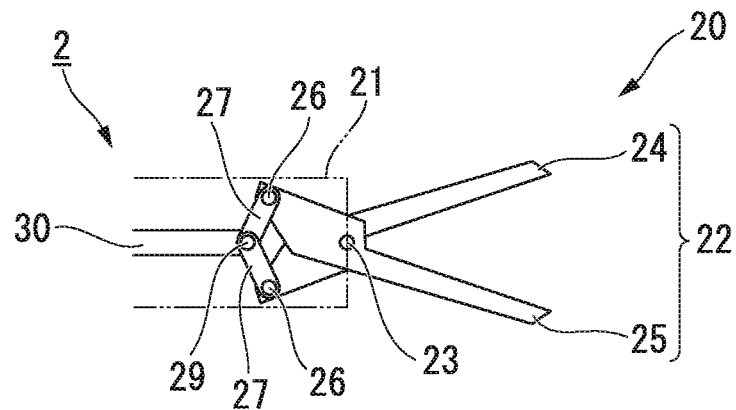
FIG. 4 is a side view showing a state in which the treatment portion of the treatment tool according to the first embodiment of the present invention is open.

When the operation rod 30 is moved (retracted) toward the proximal end with respect to the treatment insertion portion 21 as shown in FIG. 3, a distal end portion of the grasping piece 24 and a distal end portion of the grasping piece 25 are in a closed state in which the distal ends thereof come into contact with each other in the treatment portion 20 configured in this way. On the other hand, when the operation rod 30 is moved (pushed-in) toward the distal end with respect to the treatment insertion portion 21 as shown in FIG. 4, the distal end portion of the grasping piece 24 and the distal end portion of the grasping piece 25 are in an open state in which the distal ends thereof are spaced apart from each other.

An opening operation can be performed to set the open state in which the grasping pieces 24 and 25 are spaced apart from each other by pushing the operation rod 30 in, and a closing operation can be performed to set the closed state in which the grasping pieces 24 and 25 come into contact with each other by retracting the operation rod 30.

Treatment can be performed using the treatment portion 20 by setting the grasping pieces 24 and 25 to the open state or the closed state by pushing in or retracting the operation rod 30.

As shown in FIG. 1, the treatment insertion portion 21 of the treatment portion 20 is inserted into a conduit line 15a of the outer cylindrical tube 15. The grasping portion 22 of the treatment portion 20 protrudes forward from a distal end surface 15b of the outer cylindrical tube 15. The treatment portion 20 can be rotated around an axis C2 of the treatment insertion portion 21 inside the conduit line 15a of the outer cylindrical tube 15.

The treatment assisting portion 35 is operated in cooperation with the treatment portion 20 and is for the purpose of assisting an operation of the treatment portion 20 when treatment is performed using the treatment portion 20. The treatment assisting portion 35 has a first link (a link) 36, a proximal end portion of which is fixed to the distal end surface 15b of the outer cylindrical tube 15, a second link (a link) 38 which is joined to a distal end portion of the first link 36 via a first joint (a joint) 37, a third link (a link) 40 which is joined to a distal end portion of the second link 38 via a second joint (a joint) 39, and an assisting portion 41 which is attached to a distal end portion of the third link 40.

The links 36, 38, and 40 are formed in a cylindrical shape using a metal such as stainless steel. The first link 36 is fixed to the distal end surface 15b of the outer cylindrical tube 15 to extend along a longitudinal axis C1 of the outer cylindrical tube 15.

Figure 5:
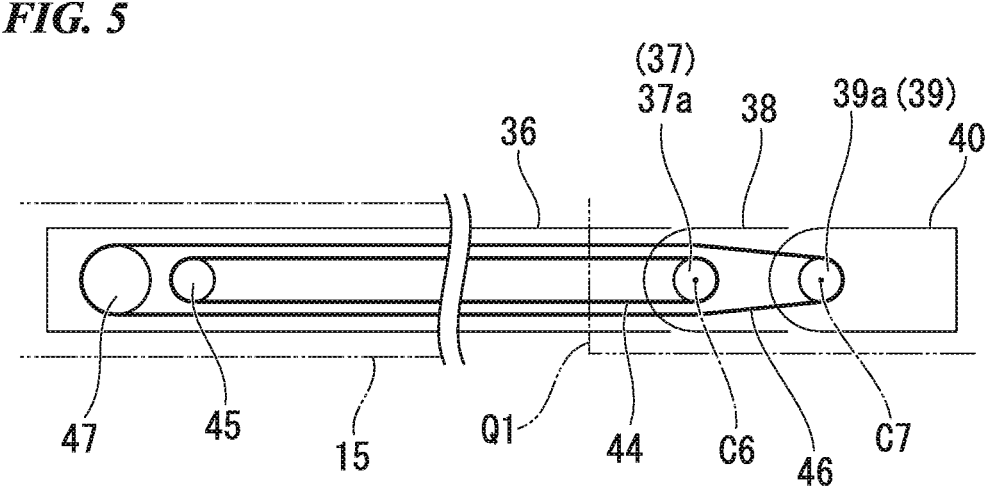
FIG. 5 is a view that schematically shows a configuration of a treatment assisting portion of the treatment tool according to the first embodiment of the present invention.

As shown in FIG. 5, a driven pulley 37a of the first joint 37 is attached to a proximal end portion of the second link 38. A distal end portion of a first wire 44 is wound around the driven pulley 37a. A driving pulley 45 is wound around a proximal end portion of the first wire 44.

Similarly, a driven pulley 39a of the second joint 39 is attached to a proximal end portion of the third link 40. A distal end portion of a second wire 46 is wound around the driven pulley 39a. A driving pulley 47 is wound around a proximal end portion of the second wire 46.

A rotating axis C6 about which the first joint 37 rotates the second link 38 with respect to the first link 36 and a rotating axis C7 about which the second joint 39 rotates the third link 40 with respect to the second link 38 are parallel to each other.

The assisting portion 41 is disposed at a distal end portion of the treatment assisting portion 35 as shown in FIG. 1 and is configured as in the grasping portion 22 of the treatment portion 20. In other words, the assisting portion 41 has a pair of assisting-portion grasping pieces 49 and 50 that are rotatably supported by pins (not shown) at the distal end portion of the third link 40. Pins, intermediate links, and an operation wire 51 (refer to FIG. 2) are joined to proximal end portions of the assisting-portion grasping pieces 49 and 50, which are not shown. The operation wire 51 extends toward the proximal end to pass through the links 36, 38, and 40. The assisting-portion grasping pieces 49 and 50 are set to the open state or the closed state by pushing in or retracting the operation wire 51 so that tissue can be grasped using the assisting portion 41.

A rotational force of the driving pulley 45 is transferred to the driven pulley 37a via the first wire 44 by rotating the driving pulley 45. The second link 38 is rotated on a plane which is perpendicular to the rotating axis C6 together with the driven pulley 37a, and an angle which is formed by the first link 36 and the second link 38 centered on the rotating axis C6 (hereinafter also referred to as an "angle formed by the first joint 37") changes. Similarly, a rotational force of the driving pulley 47 is transferred to the driven pulley 39a via the second wire 46 by rotating the driving pulley 47. The third link 40 is rotated on a plane which is perpendicular to a rotating axis C7 together with the driven pulley 39a.

As described above, the links 38 and 40 are rotated on a virtual plane Q1 that is perpendicular to the rotating axes C6 and C7 by rotating the driving pulleys 45 and 47.

In this example, the grasping pieces 24 and 25 or the assisting-portion grasping pieces 49 and 50 are moved on the virtual plane Q1 so that the grasping portion 22 or the assisting portion 41 are opened or closed. However, the grasping pieces 24 and 25 or the assisting-portion grasping pieces 49 and 50 may be moved in a direction that intersects the virtual plane Q1.

When the links 36, 38, and 40 are adjusted to be disposed on the same straight line along the longitudinal axis C1 by rotating the driving pulleys 45 and 47, the assisting portion 41 is moved to a first position R1 near the treatment portion 20 in a second direction Y which is perpendicular to the longitudinal axis C1 of the outer cylindrical tube 15. Note that the second direction Y is parallel to the virtual plane Q1.

Here, a direction that is parallel to the virtual plane Q1 and is perpendicular to the second direction Y is defined as a first direction X.

When the assisting portion 41 of the treatment assisting portion 35 is disposed at the first position, the assisting portion 41 is preferably disposed closer to a distal end than a distal end portion of the treatment portion 20.

Figure 6:
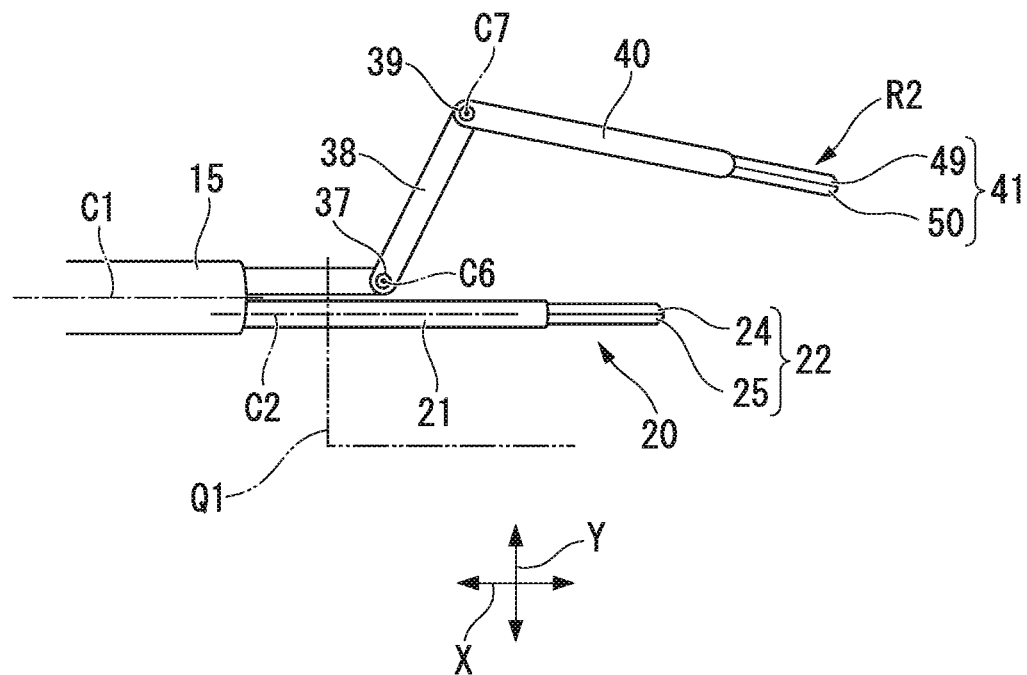
FIG. 6 is a side view showing a state in which a treatment assisting portion of the treatment tool according to the first embodiment of the present invention is moved to a second position.

On the other hand, as shown in FIG. 6, the driving pulleys 45 and 47 are rotated so that the assisting portion 41 can be moved to a second position R2 in which the assisting portion 41 is moved from the first position R1 to be spaced apart from the treatment portion 20 in the second direction Y.

Figure 7:
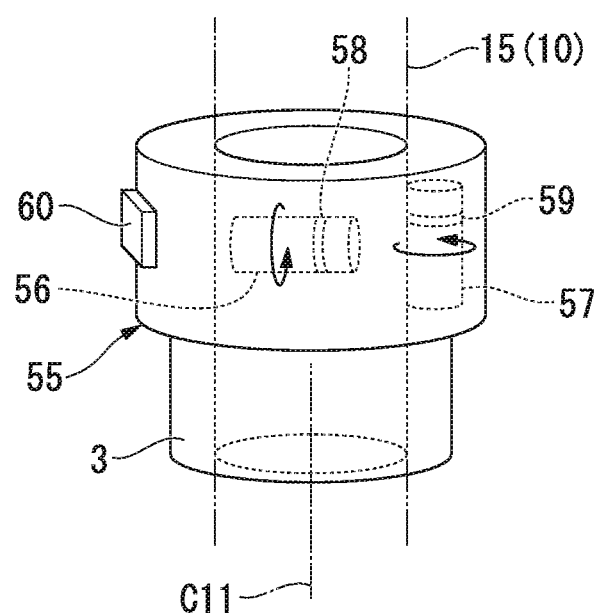
FIG. 7 is a perspective view of an operation detection portion of the treatment tool of the first embodiment of the present invention.

As shown in FIGS. 2 and 7, the operation detection portion 55 has, for example, a first roller 56 and a second roller 57 which are provided at an inner circumferential surface of the trocar 3 to be exposed, rotary encoders 58 and 59 which are attached to the first roller 56 and the second roller 57, and an acceleration sensor 60 which is attached to an outer circumferential surface of the trocar 3.

The first roller 56 is supported by the trocar 3 to be capable of being rotated around an axis which is perpendicular to an axis C11 of the trocar 3. The second roller 57 is supported by the trocar 3 to be capable of being rotated around an axis that is parallel to the axis C11 of the trocar 3.

The rotary encoder 58 determines a direction in which the first roller 56 is rotated and an amount of rotation of the first roller 56, converts the direction and the amount of rotation into signals, and transmits the signals to the control portion 80. The rotary encoder 59 determines a direction in which the second roller 57 is rotated and an amount of rotation of the second roller 57, converts the direction and the amount of rotation into signals, and transmits the signals to the control portion 80.

A sensor of a well-known method in which inclinations of two axes or more can be detected such as a capacitance type or a piezoresistance type can be used as the acceleration sensor 60. The acceleration sensor 60 determines an orientation of the trocar 3, converts the direction into a signal, and transmits the signal to the control portion 80.

In the present embodiment, when the insertion portion 10 of the treatment tool 2 is inserted into the trocar 3, the outer cylindrical tube 15 can be advanced or retracted with respect to the trocar 3 and the outer cylindrical tube 15 can be rotated around the axis C11 of the trocar 3 with respect to the trocar 3 while the axis C11 of the trocar 3 and the longitudinal axis C1 of the outer cylindrical tube 15 are maintained in a parallel state. In other words, the orientation of the trocar 3, which is detected by the acceleration sensor 60, is the same as an orientation of the outer cylindrical tube 15.

When the insertion portion 10 is inserted into the trocar 3, the first roller 56 is rotated in accordance with an amount of insertion of the insertion portion 10. The amount of movement in a direction along the longitudinal axis C1 of the outer cylindrical tube 15 with respect to the trocar 3 is detected by the rotary encoder 58.

As shown in FIG. 1, the operation portion 65 has an operation-portion main body 66 which is attached to a proximal end portion of the outer cylindrical tube 15, a driving portion 67 which is built into the operation-portion main body 66, and a treatment operation portion 68, a movement instruction portion 69, and a mode-changing switch (a mode-changing portion) 70 which are provided at an outer surface of the operation-portion main body 66.

The operation-portion main body 66 is formed with a through hole 66a. The through hole 66a is in communication with the conduit line 15a of the outer cylindrical tube 15.

As shown in FIG. 2, the driving portion 67 has a first joint driving motor 73 which is connected to the driving pulley 45, a second joint driving motor 74 which is connected to the driving pulley 47, and a grasping-portion driving motor 75 which is connected to a proximal end portion of the operation wire 51 of the treatment assisting portion 35.

The motors 73, 74, and 75 are provided with encoders 73a, 74a, and 75a which detect the number of revolutions of rotating shafts of the motors 73, 74, and 75, respectively.

The driving pulleys 45 and 47 can be rotated in a desired direction by driving the joint driving motors 73 and 74. Thus, the links 38 and 40 are rotated on the virtual plane Q1, and the assisting portion 41 of the treatment assisting portion 35 is thus moved. The assisting portion 41 can be moved between the first position and the second position, which have been described, above by driving the joint driving motors 73 and 74.

The operation wire 51 is advance or retracted with respect to the links 36, 38, and 40 by driving the grasping-portion driving motor 75, and the assisting portion 41 can thus be opened or closed.

Figure 8:
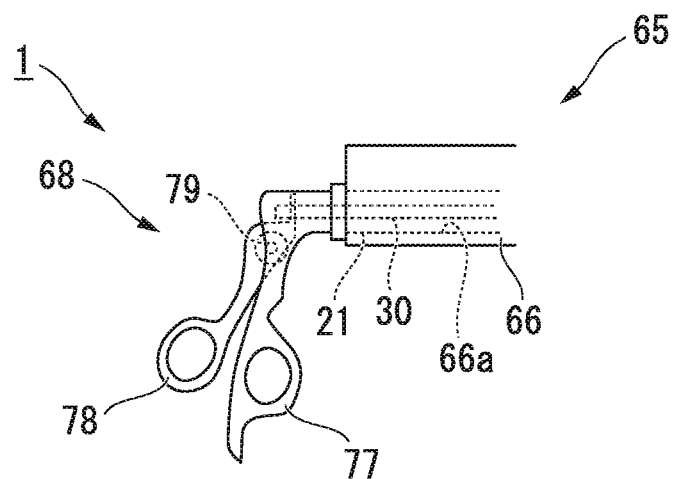
FIG. 8 is a side view when a treatment operation portion of the treatment tool according to the first embodiment of the present invention is closed.

As shown in FIGS. 1 and 8, the treatment operation portion 68 is attached to a proximal end portion of the treatment insertion portion 21 which is inserted into the conduit line 15a of the outer cylindrical tube 15 and the through hole 66a of the operation-portion main body 66. The treatment operation portion 68 has a grip 77 which is attached to the proximal end portion of the treatment insertion portion 21, a lever 78, one end of which is rotatably supported by the grip 77, and a rotary encoder 79 which determines an angle formed by the grip 77 and the lever 78.

A proximal end portion of the operation rod 30 is attached to a distal end portion of the lever 78.

Figure 9:
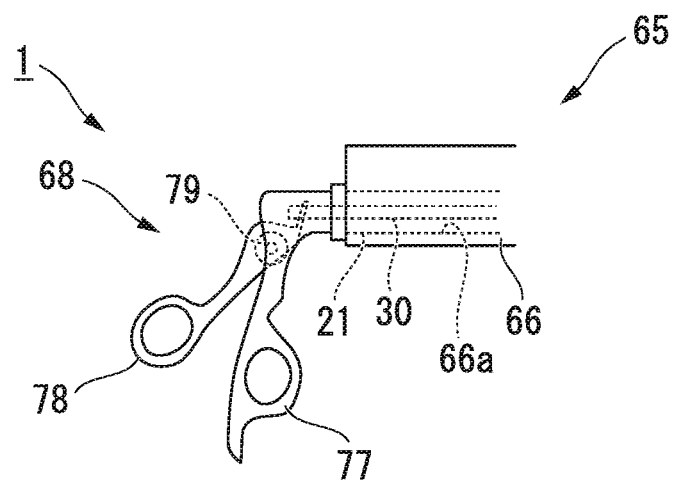
FIG. 9 is a side view when the treatment operation portion of the treatment tool according to the first embodiment of the present invention is open.

As shown in FIG. 8, when the treatment operation portion 68 is closed by bringing a proximal end portion of the lever 78 into contact with a proximal end portion of the grip 77, the operation rod 30 is retracted, and thus the grasping portion 22 is in the closed state shown in FIG. 3. On the other hand, as shown in FIG. 9, when the treatment operation portion 68 is opened by causing the proximal end portion of the lever 78 to be spaced apart from the proximal end portion of the grip 77, the operation rod 30 is pushed in, and thus the grasping portion 22 is in the open state shown in FIG. 4. As described above, the treatment operation portion 68 opens or closes the grasping pieces 24 and 25 of the grasping portion 22 of the treatment portion 20.

The rotary encoder 79 converts the detected angle into a signal and transmits the signal to the control portion 80 (refer to FIG. 2).

The grip 77 is joined to the operation-portion main body 66. The treatment portion 20 can be rotated around the axis C2 inside the conduit line 15a of the outer cylindrical tube 15 and the through hole 66a of the operation-portion main body 66 in a state in which treatment portion 20 is integrally formed with the treatment operation portion 68.

The movement instruction portion 69 is, for example, an input portion of a joystick type. As shown in FIG. 1, the movement instruction portion 69 can be moved in a first indication direction D and a second indication direction E which are perpendicular to each other about a reference position of the movement instruction portion 69 with respect to an operation surface 66b which is defined on a lateral surface of the operation-portion main body 66. Movement of the treatment assisting portion 35 on the virtual plane Q1 in the first direction X and the second direction Y to response to the movement of the movement instruction portion 69 in the first indication direction D or the second indication direction E will be described below.

The movement instruction portion 69 determines an input by an operator and transmits the detection result to the control portion 80.

A mode-changing switch 70 is a switch of a push button type. The mode-changing switch 70 has a spring member (not shown). In a state in which the mode-changing switch 70 is not pushed in, the mode-changing switch 70 protrudes from the operation-portion main body 66 by an elastic force of the spring member. The mode-changing switch 70 can be pushed against the elastic force of the spring member toward the operation-portion main body 66.

As will be described below, the control portion 80 has a first mode and a second mode as a control mode. In the state in which the mode-changing switch 70 is not pushed in, the control mode of the control portion 80 is the first mode. The control mode of the control portion 80 is the second mode while the mode-changing switch 70 is pushed in. The mode-changing switch 70 switches the control mode of the control portion 80 between the first mode and the second mode.

As shown in FIG. 2, the control portion 80 has a calculating device 82 and a memory 83 which are connected to a bus 81.

The rotary encoders 58 and 59 and the acceleration sensor 60 of the operation detection portion 55, the motors 73, 74, and 75 and the encoders 73a, 74a, and 75a of the driving portion 67, the rotary encoder 79 of the treatment operation portion 68, the movement instruction portion 69, and the mode-changing switch 70 are connected to the bus 81.

The memory 83 stores a control program for controlling the calculating device 82, lengths of the links 36, 38, and 40 of the treatment tool 2, a length of the assisting portion 41, and the like.

The control portion 80 has the first mode in which the driving portion 67 is controlled based on the detection result transmitted from the movement instruction portion 69 and the second mode in which the driving portion 67 is controlled based on the detection result transmitted from the operation detection portion 55 as the control mode. In other words, the control portion 80 moves the assisting portion 41 of the treatment assisting portion 35 based on an operation of the movement instruction portion 69 by the operator in the first mode, but automatically moves the assisting portion 41 based on the detection result of the operation detection portion 55 in the second mode.

Hereinafter, first, movement control and opening or closing operation control of the assisting portion 41 when the control mode is the first mode will be described.

Figure 10:
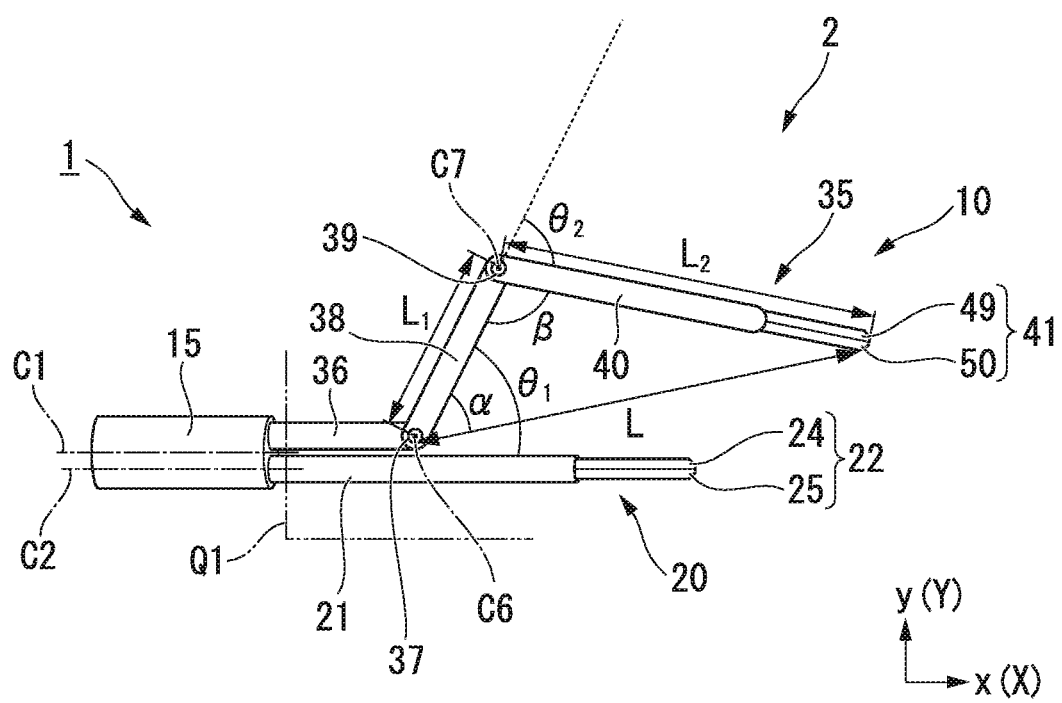
FIG. 10 is a view showing a method of controlling an angle of a joint when a control mode of the treatment tool according to the first embodiment of the present invention is a first mode.

As shown in FIG. 10, an x-axis is defined parallel to the first direction X on the virtual plane Q1, and a distal end side in the first direction X is a positive direction of the x-axis. A y-axis is defined parallel to the second direction Y, the treatment assisting portion 35 side with respect to the treatment portion 20 in the second direction Y is a positive direction of the y-axis.

A position of the rotating axis C6 of the first joint 37 is set as an origin of the x-axis and the y-axis, and coordinates of a distal end of the assisting portion 41 are set as $(x_2, y_2)$.

A distance between the rotating axis C6 of the first joint 37 and the rotating axis C7 of the second joint 39 is set as $L_1$, a distance between the rotating axis C7 of the second joint 39 and the distal end of the assisting portion 41 is set as $L_2$, and a distance between the rotating axis C6 of the first joint 37 and the distal end of the assisting portion 41 is set as L. An angle that is formed by a line connecting the rotating axis C6 of the first joint 37 to the distal end of the assisting portion 41 and the second link 38 is set as a. Note that, hereinafter, all angles are in a portion of radians.

An angle that is formed by the second link 38 and the third link 40 is set as β. An angle that is formed by the second link 38 and the treatment insertion portion 21 is set as $\theta_1$. A supplementary angle of the angle β is set as $\theta_2$.

The operator moves the movement instruction portion 69 from the reference position of the movement instruction portion 69 in the first indication direction D or the second indication direction E so that an amount of movement in the x-axis and the y-axis of the distal end of the assisting portion 41 is designated as $(x_2, y_2)$.

At this time, Expressions (1) to (3) are accomplished based on the cosine theorem and the like. An angle which is formed by the joints 37 and 39 is adjusted as in Expressions (4) and (5), which are induced from Expressions (1) to (3), so that the distal end of the assisting portion 41 can be disposed at the coordinates $(x_2, y_2)$.

[Math. 1]

$$L_2^2 = L_1^2 + L^2 - 2L_1 L \cos\alpha \quad (1)$$

$$L^2 = L_1^2 + L_2^2 - 2L_1 L_2 \cos\beta \quad (2)$$

$$L^2 = x_2^2 + y_2^2 \quad (3)$$

$$\theta_1 = \alpha + \tan\frac{y_2}{x_2} \quad (4)$$

$$\theta_2 = \pi - \beta \quad (5)$$

Note that, when coordinates are the coordinates $(x_2, y_2)$ of the distal end of the assisting portion 41 at which the distal end thereof cannot reach due to the configuration of the treatment assisting portion 35, for example, the distal end of the assisting portion 41 is moved to a position at which the distal end of the assisting portion 41 can reach and which is closest to the coordinates $(x_2, y_2)$.

Hereinafter, description will be given using a specific example.

As an initial state, as shown in FIG. 1, a shape of the treatment assisting portion 35 is set to be a shape B1 in which the links 36, 38, and 40 are disposed on the same straight line along the longitudinal axis C1.

Figure 11:
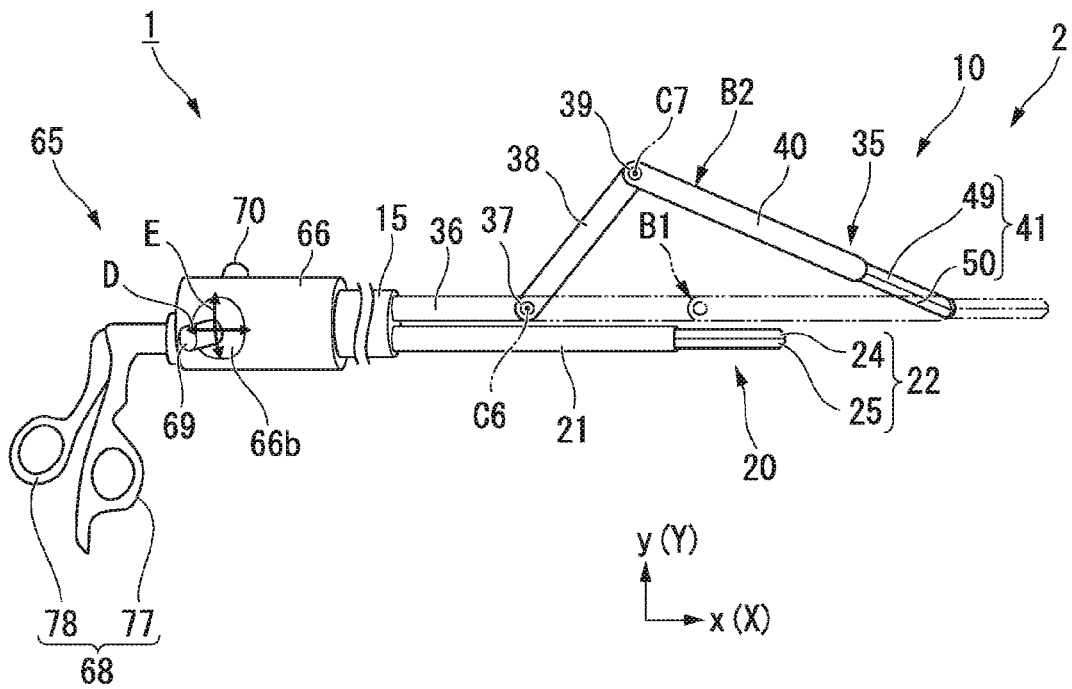
FIG. 11 is a view showing a motion of the treatment assisting portion when the control mode of the treatment tool according to the first embodiment of the present invention is the first mode.

As shown in FIG. 11, when the movement instruction portion 69 is moved from this state toward the proximal end with respect to the operation surface 66b in the first indication direction D, the control portion 80 moves the assisting portion 41 of the treatment assisting portion 35 toward the proximal end in the first direction X with respect to a proximal end portion of the treatment assisting portion 35 based on the detection result transmitted from the movement instruction portion 69. The shape of the treatment assisting portion 35 in this state is set to be a shape B2. Note that the shape B1 of the treatment assisting portion 35 in FIG. 11 is indicated using a two-dot chain line.

Figure 12:
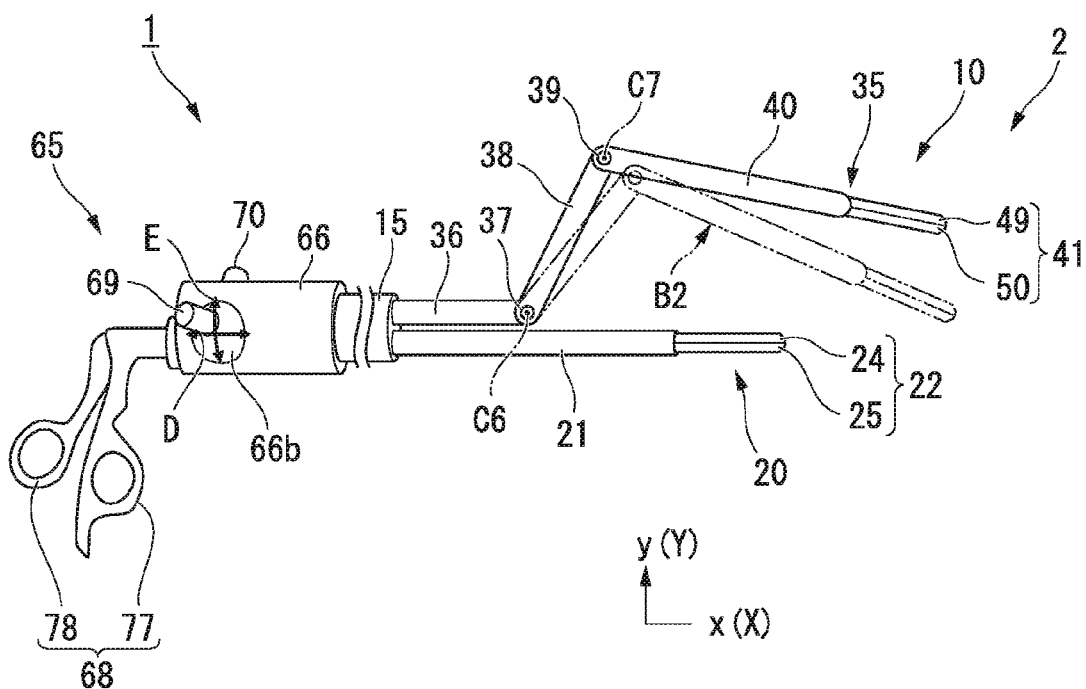
FIG. 12 is a view showing a motion of the treatment assisting portion when the control mode of the treatment tool according to the first embodiment of the present invention is the first mode.

Also, when the movement instruction portion 69 is moved to one side in the second indication direction E with respect to the operation surface 66b as shown in FIG. 12 from a state in which the treatment assisting portion 35 has the shape B2, the control portion 80 moves the assisting portion 41 of the treatment assisting portion 35 with respect to the proximal end portion of the treatment assisting portion 35 to one side in the second direction Y. Note that the shape B2 of the treatment assisting portion 35 in FIG. 12 is indicated using a two-dot chain line.

As described above, the assisting portion 41 of the treatment assisting portion 35 can be moved with respect to the proximal end portion of the treatment assisting portion 35 in the first direction X and the second direction Y.

When the control mode is the first mode, if the rotary encoder 79 determines the closing of the treatment operation portion 68, the grasping portion 22 is closed, and simultaneously the control portion 80 closes the assisting portion 41 by driving the grasping-portion driving motor 75. Similarly, if the rotary encoder 79 determines the opening of the treatment operation portion 68, the grasping portion 22 is opened, and simultaneously the grasping-portion driving motor 75 is driven to open the assisting portion 41.

Next, movement control and opening or closing operation control of the assisting portion 41 when the control mode is the second mode will be described.

Figure 13:
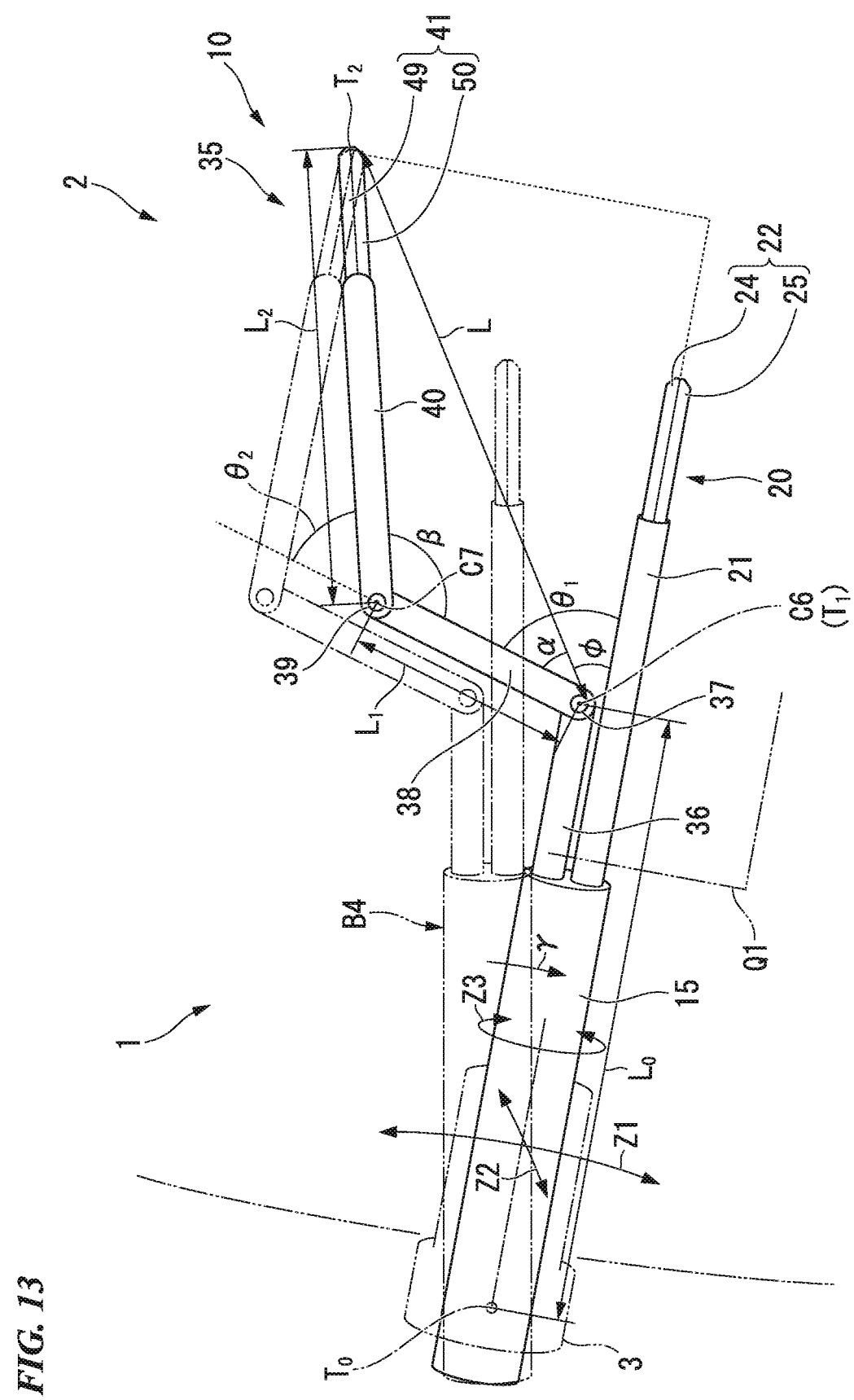
FIG. 13 is a view showing a method of controlling an angle of a joint when the control mode of the treatment tool according to the first embodiment of the present invention is a second mode.

As shown in FIG. 13, the trocar 3 and the treatment tool 2 are assumed to be rotated an angle γ around a point $T_0$ serving as a center of the trocar 3 along the virtual plane Q1 from a shape B4 of the treatment tool system 1 which is indicated using a two-dot chain line. Note that, in the following example, a length $L_5$ to which the outer cylindrical tube 15 is pushed in with respect to the trocar 3 is set to be 0.

At this time, the control portion 80 controls the driving portion 67 such that a distance between the treatment portion 20 and the assisting portion 41 of the treatment assisting portion 35 is not a predetermined distance or less. To be more specific, the control portion 80 controls the driving portion 67 such that a position of the assisting portion 41 of the treatment assisting portion 35 is not moved. Note that the fact that the position of the assisting portion 41 is not moved which is described herein refers to the fact that the position of the assisting portion 41 is not moved when the operator rotates the treatment tool system 1 only on the virtual plane Q1 (rotation of a pitch direction Z1), but rotation of a yaw direction Z2 or a roll direction Z3 is not considered.

The length $L_5$ to which the outer cylindrical tube 15 is pushed in with respect to the trocar 3 corresponds to an amount of movement of the outer cylindrical tube 15 with respect to the trocar 3, and the angle γ by which the trocar 3 and the treatment tool 2 are rotated corresponds to the orientation of the outer cylindrical tube 15.

A distance that is defined in advance is added to $L_1$ or the angle α, a distance between the point $T_0$ of the trocar 3 and the rotating axis C6 of the first joint 37 is set as $L_0$, and an angle obtained by subtracting the angle α from the angle $\theta_1$ is set as φ.

When a position of the point $T_0$ of the trocar 3 is set as the origin of the x-axis and the y-axis, coordinates of a point $T_1$ that is at the rotating axis C6 of the first joint 37 are represented by Expression (6).

$$(L_0 \cos\gamma, -L_0 \sin\gamma) \quad (6)$$

When coordinates of a point $T_2$ serving as the distal end of the assisting portion 41 are set as $(x_2, y_2)$, Expressions (7) to (9) are accomplished. An angle that is formed by the joints 37 and 39 is adjusted as in Expression (10) to Expression (12), which are induced from Expression (7) to Expression (9), so that control can be performed such that a position of the assisting portion 41 is not moved.

[Math. 2]

$$L_2^2 = L_1^2 + L^2 - 2L_1 L \cos\alpha \qquad (7)$$

$$L^2 = L_1^2 + L_2^2 - 2L_1 L_2 \cos\beta \qquad (8)$$

$$L^2 = x_2^2 + y_2^2 \qquad (9)$$

$$\theta_1 = \alpha + \phi \qquad (10)$$

$$\phi = \cos^{-1} \frac{\overrightarrow{T_0 T_1} \cdot \overrightarrow{T_1 T_2}}{|\overrightarrow{T_0 T_1}||\overrightarrow{T_1 T_2}|} \qquad (11)$$

$$\theta_2 = \pi - \beta \qquad (12)$$

When the control mode is the second mode, the assisting portion 41 cannot be opened or closed even if the treatment operation portion 68 is closed or opened.

The control portion 80 performs control such that the rotating shafts of the driving motors 73, 74, and 75 are at predetermined rotational angles based on signals transmitted from the encoders 73a, 74a, and 75a.

Figure 14:
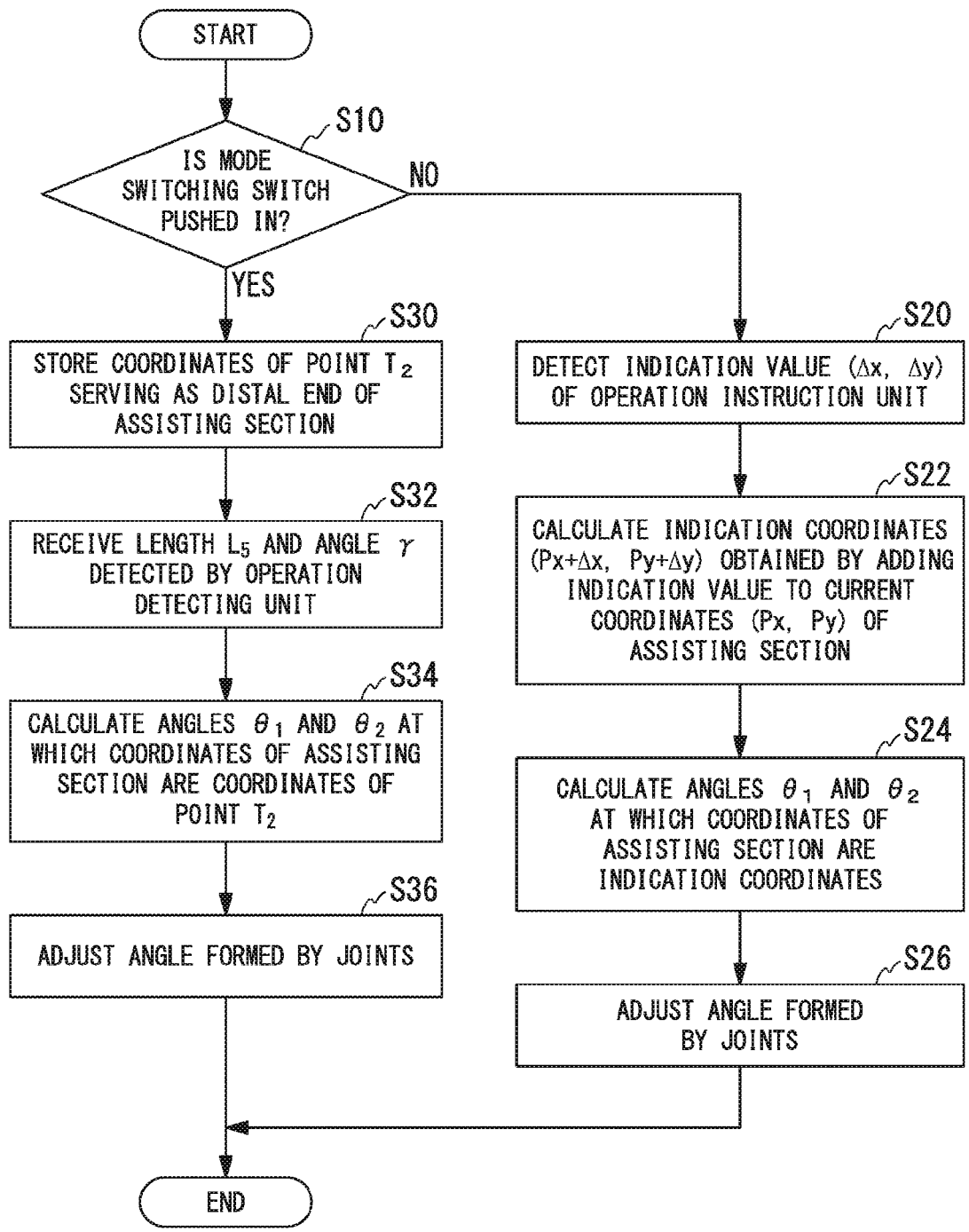
FIG. 14 is a flowchart showing a procedure in which treatment is performed in the treatment tool system according to the first embodiment of the present invention.

Next, an action of the treatment tool system 1 configured as described above will be described. Hereinafter, a case in which treatment is performed through a hole that is formed in an abdominal wall of a patient will be described. FIG. 14 is a flowchart showing a procedure by which the treatment is performed in the treatment tool system 1 according to the present embodiment. Note that, in the treatment tool 2, the assisting portion 41 is disposed at the first position near the treatment portion 20 in the second direction Y in advance and the grasping portion 22 and the assisting portion 41 are closed. In FIGS. 15 to 19, the control portion 80 is not shown.

Figure 15:
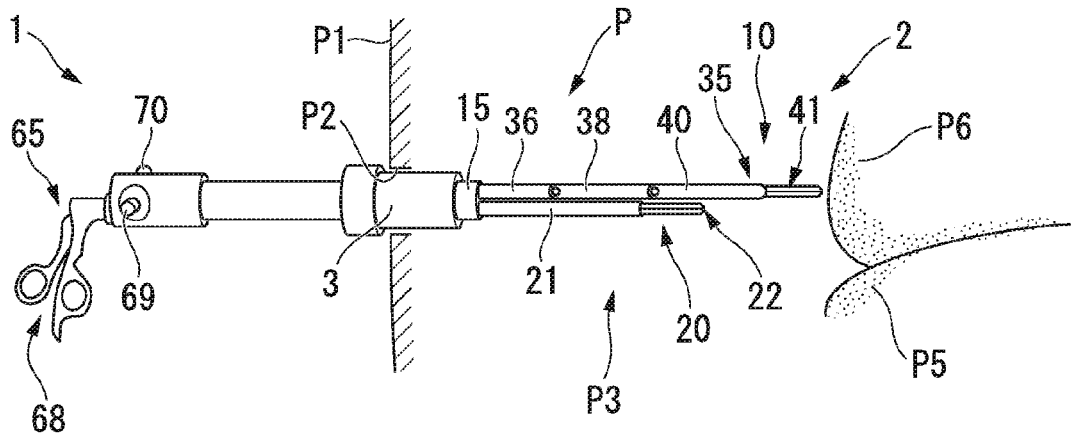
FIG. 15 is a view showing a procedure of treatment using the treatment tool system according to the first embodiment of the present invention.

As shown in FIG. 15, an operator such as a surgeon forms a hole P2 by cutting an abdominal wall P1 of a patient P. The trocar 3 is attached to the hole P2.

When the treatment tool 2 is activated, it is determined whether the mode-changing switch 70 is pushed in in Step S10 of FIG. 14. Here, since the mode-changing switch 70 is not pushed in, NO is determined in Step S10, and the process proceeds to Step S20.

At this time, the control mode of the control portion 80 is the first mode.

The operator grasps the treatment operation portion 68 of the operation portion 65 with one hand and inserts the insertion portion 10 of the treatment tool 2 into the trocar 3. At this time, the rollers 56 and 57 are rotated, the amount of movement of the outer cylindrical tube 15 with respect to the trocar 3 is detected by the rotary encoders 58 and 59 of the operation detection portion 55, and an orientation of the outer cylindrical tube 15 is detected by the acceleration sensor 60. The operation detection portion 55 transmits the detection result to the control portion 80 at predetermined time intervals.

The calculating device 82 of the control portion 80 calculates coordinates (Px, Py) of the assisting portion 41 at predetermined time intervals from an integrated value of the amount of movement of the outer cylindrical tube 15 transmitted from the operation detection portion 55 and lengths and the like of the links 36, 38, and 40 stored in the memory 83.

The assisting portion 41 is brought into contact with an organ P6 which is adjacent to an organ (tissue) P5 serving as a treatment target while observing the insertion portion 10 of the treatment tool 2 using a laparoscope (not shown) which is inserted into an abdominal cavity P3 through a separate passage from the hole P2.

Figure 16:
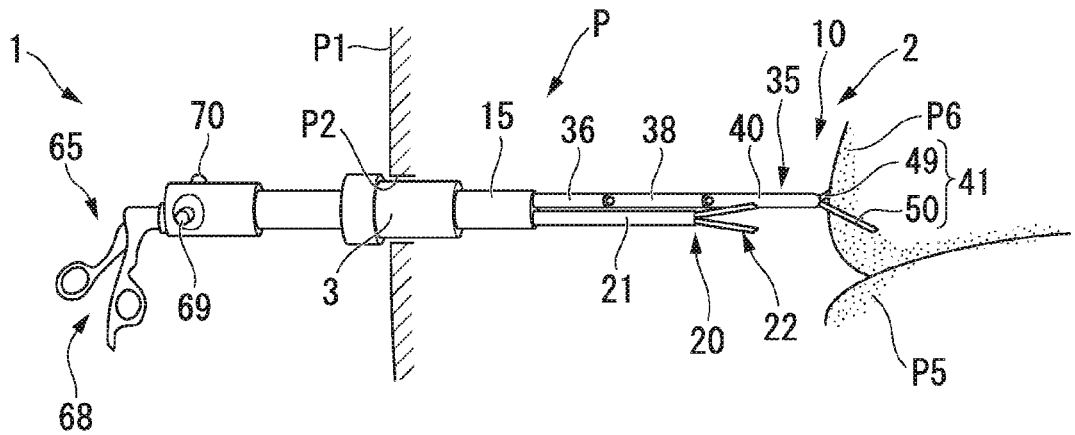
FIG. 16 is a view showing a procedure of treatment using the treatment tool system according to the first embodiment of the present invention.

As shown in FIG. 16, the grasping portion 22 and the assisting portion 41 are set to the open state by opening the treatment operation portion 68. The assisting-portion grasping pieces 49 and 50 of the assisting portion 41 are pressed against the organ P6 by pushing in the operation portion 65. Since the assisting portion 41 is disposed closer to the distal end side than the grasping portion 22, the grasping portion 22 does not interfere when the organ P6 is grasped by the assisting portion 41.

The grasping portion 22 and the assisting portion 41 are set to the closed state by closing the treatment operation portion 68, and the organ P6 is thus grasped by the assisting portion 41.

Figure 17:
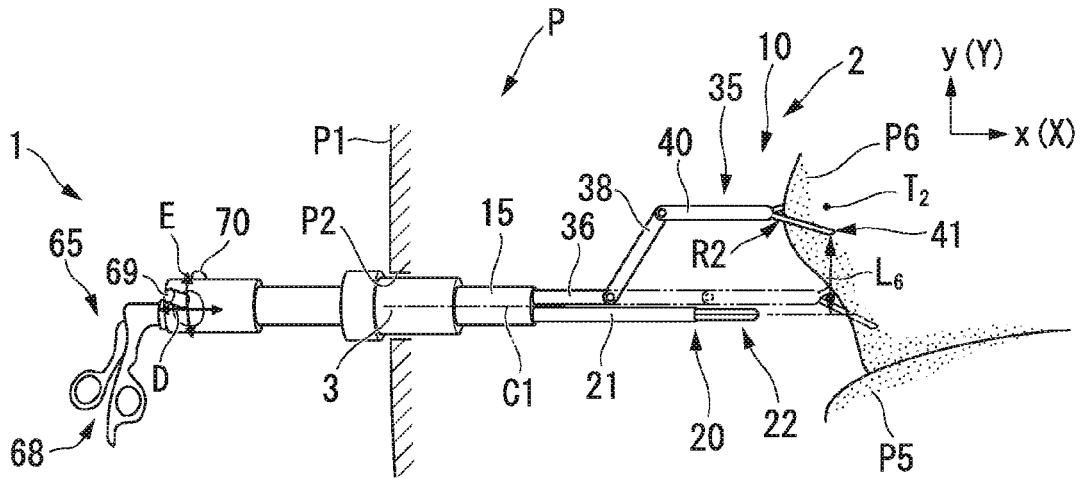
FIG. 17 is a view showing a procedure of treatment using the treatment tool system according to the first embodiment of the present invention.

Here, as shown in FIG. 17, the operator moves the assisting portion 41 by operating the movement instruction portion 69. To be more specific, the operator moves the movement instruction portion 69 with his/her other hand in the first indication direction D or the second indication direction E. The movement instruction portion 69 determines an indication value Δx in an x-axis which corresponds to an amount of movement of the movement instruction portion 69 in the first indication direction D and an indication value Δy in a y-axis which corresponds to an amount of movement thereof in the second indication direction E, converts the detected indication values into signals, and transmits the signals to the control portion 80. The control portion 80 determines an indication value (Δx, Δy) transmitted from the movement instruction portion 69 in Step S20, and the process proceeds to Step S22.

In Step S22, the calculating device 82 of the control portion 80 calculates indication coordinates (Px+Δx, Py+Δy) obtained by adding the indication value (Δx, Δy) to current coordinates (Px, Py) of the assisting portion 41, and the process proceeds to Step S24.

In Step S24, the calculating device 82 calculates the angles $\theta_1$ and $\theta_2$ based on Expression (4) and Expression (5) described above such that the coordinates of the assisting portion 41 are the indication coordinates, and the process proceeds to Step S26.

In Step S26, the calculating device 82 drives the joint driving motors 73 and 74 of the driving portion 67 and adjusts the angle that is formed by the joints 37 and 39. Here, all of the steps end.

In a state in which the mode-changing switch 70 is not pushed in, for example, Step S10 and Steps S20 to S26 described above are repeated a plurality of times so that the assisting portion 41 is moved to the second position R2.

At this time, the organ P6 is pulled away from the organ P5 so that traction acts between the organ P5 and the organ P6, and the organ P6 is pulled by the assisting portion 41.

Here, the operator continues to push in the mode-changing switch 70 with his/her one hand.

In Step S10, it is determined whether the mode-changing switch 70 is pushed in. Since the mode-changing switch 70 is pushed in, YES is determined in Step S10, and the process proceeds to Step S30. At this time, the control mode of the control portion 80 is the second mode.

Figure 18:
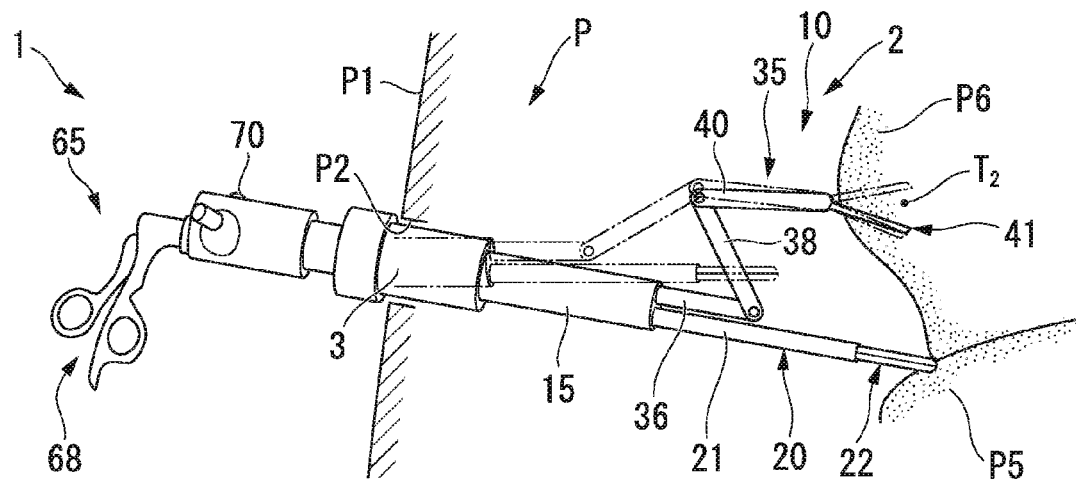
FIG. 18 is a view showing a procedure of treatment using the treatment tool system according to the first embodiment of the present invention.

Here, as shown in FIG. 18, the operator presses the grasping portion 22 against the organ P5 by pushing in the treatment tool 2.

As a specific step, in Step S30, the calculating device 82 of the control portion 80 stores coordinates of the point $T_2$ serving as the distal end of the assisting portion 41 shown in FIG. 17 in the memory 83, and the process proceeds to Step S32.

In Step S32, the calculating device 82 receives the length $L_5$ to which the outer cylindrical tube 15 is pushed in and the angle γ by which the treatment tool 2 is rotated which are transmitted from the operation detection portion 55, and the process proceeds to Step S34.

In Step S34, the calculating device 82 calculates the angles $\theta_1$ and $\theta_2$ based on Expression (10) to Expression (12) described above such that the coordinates of the assisting portion 41 are the coordinates of the point $T_2$ stored in the memory 83, and the process proceeds to Step S36.

In Step S36, the calculating device 82 drives the joint driving motors 73 and 74 of the driving portion 67 and adjusts the angle formed by the joints 37 and 39. Here, all of the steps end.

In a state in which the mode-changing switch 70 is pushed in, for example, Step S10 and Steps S30 to S36 described above are repeated a plurality of times so that the grasping portion 22 is inserted up to a position which is closer to the distal end side than the assisting portion 41 without moving the position of the assisting portion 41.

At this time, the organ P6 is pulled farther away and is detached from the organ P5.

Figure 19:
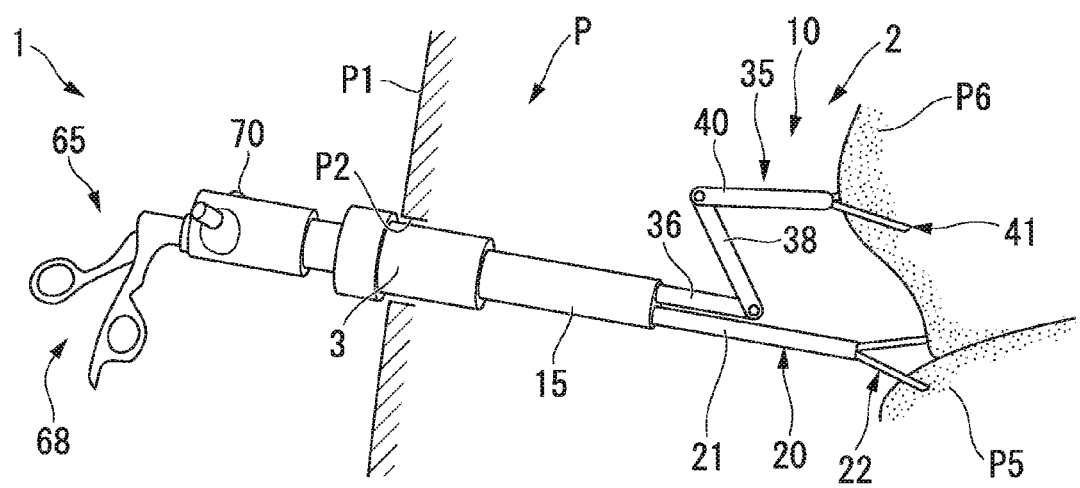
FIG. 19 is a view showing a procedure of treatment using the treatment tool system according to the first embodiment of the present invention.

Here, as shown in FIG. 19, treatment is performed on the organ P5 by opening the treatment operation portion 68 and opening the grasping portion 22.

Note that, in FIG. 17, the above-described predetermined distance refers to a length $L_6$. The distance between the treatment portion 20 and the assisting portion 41 is not the length $L_6$ or less even if the treatment tool 2 is pushed in along the longitudinal axis C1 from the state of FIG. 17.

When the control mode of the control portion 80 is the second mode, the other hand of the operator is not used to operate the treatment tool system 1. For this reason, the operator can operate a separate treatment tool from the treatment tool 2 to largely displace the organ P6 while holding the separate treatment tool with his/her other hand.

Also, when there is no need to largely displace the organ P6, the operator himself/herself can independently perform a procedure while holding the laparoscope.

As described above, according to the treatment tool 2 and the treatment tool system 1 according to the present embodiment, in a state in which the treatment assisting portion 35 is disposed at the first position R1, the treatment portion 20 and the treatment assisting portion 35 are inserted into the abdominal cavity P3 via one trocar 3. Therefore, the number of holes P2 that are formed in the abdominal wall P1 is decreased to a minimum and can be one for the purpose of being used for the treatment portion 20 and the treatment assisting portion 35, and the treatment can be performed.

Also, since the insertion portion 10 of the treatment tool 2 has two so-called treatment portions such as the treatment portion 20 and the treatment assisting portion 35, a cooperation (switching) operation between the treatment portions can be smoothly performed.

When the control mode is the first mode, the operator moves the assisting portion 41 by operating the movement instruction portion 69, and when the control mode is the second mode, the assisting portion 41 is automatically moved based on the detection result of the operation detection portion 55. For this reason, an operation to be performed by the operator is easily performed by setting the control mode to the second mode, and the operator himself/herself can move the assisting portion 41 by setting the control mode to the first mode as necessary.

The distance between the treatment portion 20 and the assisting portion 41 is not the length $L_6$ or less so that traction can reliably act between the organ P5 and the organ P6.

When the control mode is the second mode, the control portion 80 controls the driving portion 67 such that the position of the assisting portion 41 is not moved. Thus, when the grasping portion 22 is inserted up to the position that is closer to the distal end side than the assisting portion 41, greater traction can act between the organ P5 and the organ P6.

The rotating axes C6 and C7 of the joints 37 and 39 are parallel to each other so that the assisting portion 41 is moved on the virtual plane Q1, and the calculation in which the coordinates of the assisting portion 41 are acquired is easily performed.

Note that, in the present embodiment, the treatment tool 2 may have the operation detection portion 55. In this case, the operation detection portion 55 of the treatment tool 2 is attached to a well-known trocar and is used.

(Second Embodiment)

Next, a second embodiment of the present invention will be described with reference to FIGS. 2 and 20, but the same parts as those of the above-described embodiment are denoted with the same reference numerals, overlapping descriptions will be omitted, and only a difference will be described.

Figure 20:
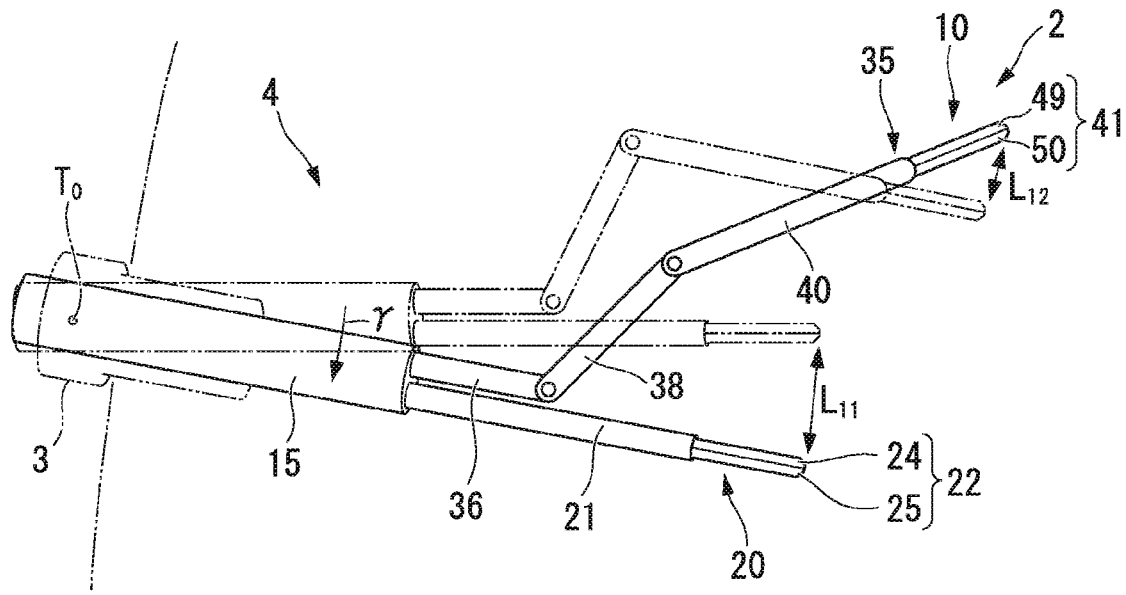
FIG. 20 is a view showing a procedure of treatment using a treatment tool system according to a second embodiment of the present invention.

As shown in FIGS. 2 and 20, a treatment tool system 4 according to the present embodiment has a control portion 85 instead of the control portion 80 of the treatment tool system 1 of the first embodiment.

The control portion 85 is different from the control portion 80 in that control content of the control portion when the control mode is the second mode differs. The control portion 85 controls a driving portion 67 such that, in the second mode, an assisting portion 41 of a treatment assisting portion 35 is moved in a direction which is opposite to a direction in which a grasping portion 22 of a treatment portion 20 is moved. Note that this control is preferably performed only when the grasping portion 22 is moved to be spaced apart from the assisting portion 41.

A distance $L_{12}$ in which the assisting portion 41 is moved with respect to a distance $L_{11}$ in which the grasping portion 22 is moved is preferably a value of 1 or less or 0 or more.

According to the treatment tool system 4 configured in this way, treatment is performed while the number of holes P2 that are formed in an abdominal wall P1 is decreased to a minimum, and a cooperation operation of a plurality of treatment portions can thus be smoothly performed.

Also, when a treatment tool 2 is rotated an angle γ around a point $T_0$ serving as a center of a trocar 3, the grasping portion 22 and the assisting portion 41 are more largely opened. Therefore, greater traction can act on an organ P6 that is grasped by the assisting portion 41 even with the same amount of operation.

(Third Embodiment)

Next, a third embodiment of the present invention will be described with reference to FIGS. 21 and 22, but the same parts as those of the above-described embodiment are denoted with the same reference numerals, overlapping descriptions will be omitted, and only differences will be described.

Figure 21:
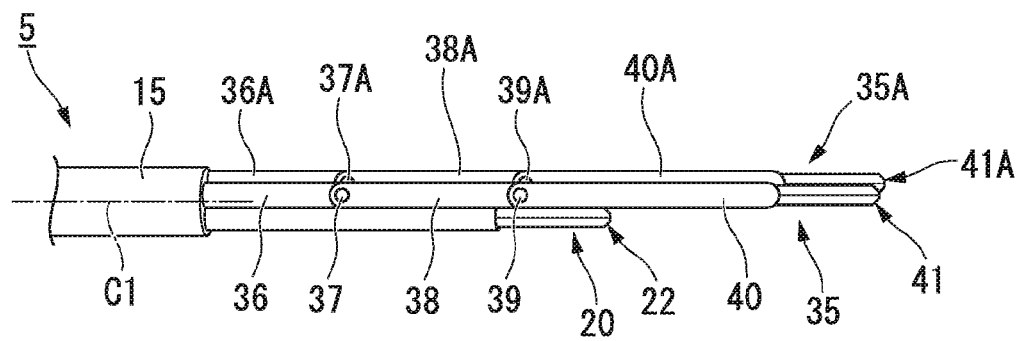
FIG. 21 is a side view of a distal end side of a treatment tool system according to a third embodiment of the present invention.

As shown in FIG. 21, a treatment tool system 5 according to the present embodiment has a second treatment assisting portion 35A which is disposed at a distal end portion of an outer cylindrical tube 15 in addition to configurations of the treatment tool system 1 of the first embodiment. The second treatment assisting portion 35A has the same configuration as the treatment assisting portion 35, and has links 36A, 38A, and 40A, joints 37A and 39A, and an assisting portion 41A which have the same configurations as the links 36, 38, and 40, the joints 37 and 39, and the assisting portion 41.

Figure 22:
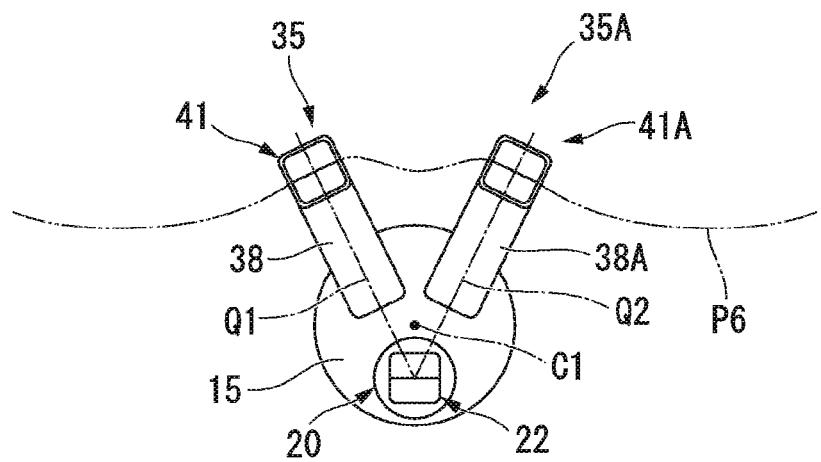
FIG. 22 is a front view of a state in which a link of the treatment tool system according to the third embodiment of the present invention is bent.

The second link 38A and the third link 40A are pivoted on a virtual plane Q2 shown in FIG. 22. The virtual plane Q2 intersects a virtual plane Q1 on which the second link 38 and the third link 40 are pivoted. To be more specific, the virtual planes Q1 and Q2 are parallel to a longitudinal axis C1 of the outer cylindrical tube 15 and intersect to be separated from each other as the planes are spaced apart from the longitudinal axis C1.

In the present embodiment, a control portion has a first mode, a second mode, and a third mode as a control mode. The treatment assisting portion 35 can be operated by a movement instruction portion 69 in the first mode, and the treatment assisting portion 35A can be operated by the movement instruction portion 69 in the second mode.

Also, in the third mode, control is performed such that positions of the assisting portion 41 and 41A are not moved.

As a mode-changing switch of the present embodiment, a switch in which the control mode is switched to the first mode, the second mode, the third mode, the first mode, . . . , for example, every time the mode-changing switch is pressed is used.

According to the treatment tool system 4 configured in this way, when an organ P6 is grasped by the assisting portions 41 and 41A in a state in which the assisting portions 41 and 41A are disposed at a second position R2, the organ P6 can be widely grasped in a direction which intersects the longitudinal axis C1.

(Fourth Embodiment)

Next, a fourth embodiment of the present invention will be described with reference to FIGS. 23 and 24, but the same parts as those of the above-described embodiment are denoted with the same reference numerals, overlapping descriptions will be omitted, and only a difference will be described.

Figure 23:
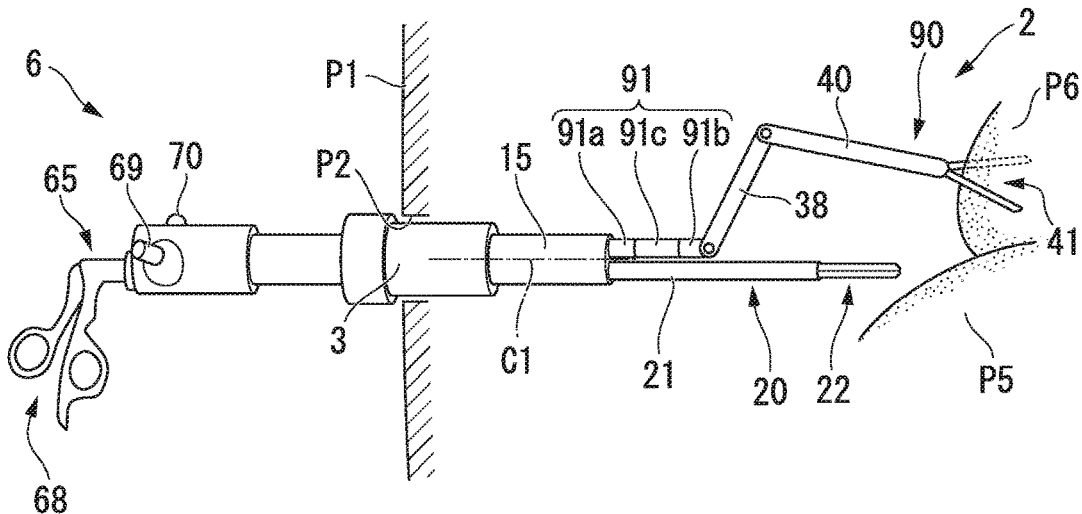
FIG. 23 is a view showing a procedure of treatment using a treatment tool system according to a fourth embodiment of the present invention.

As shown in FIG. 23, a treatment tool system 6 according to the present embodiment has a treatment assisting portion 90 instead of the treatment assisting portion 35 of the treatment tool system 1 of the first embodiment. The treatment assisting portion 90 has a first link (a link and a proximal end link) 91 instead of the first link 36 of the treatment assisting portion 35.

The first link 91 has a rotating portion 91c by which a link piece 91b serving as a distal end side of the first link 91 is rotated around a longitudinal axis of the first link 91 with respect to a link piece 91a serving as a proximal end side of the first link 91. The rotating portion 91c can be configured by a well-known rotary joint or the like.

Figure 24:
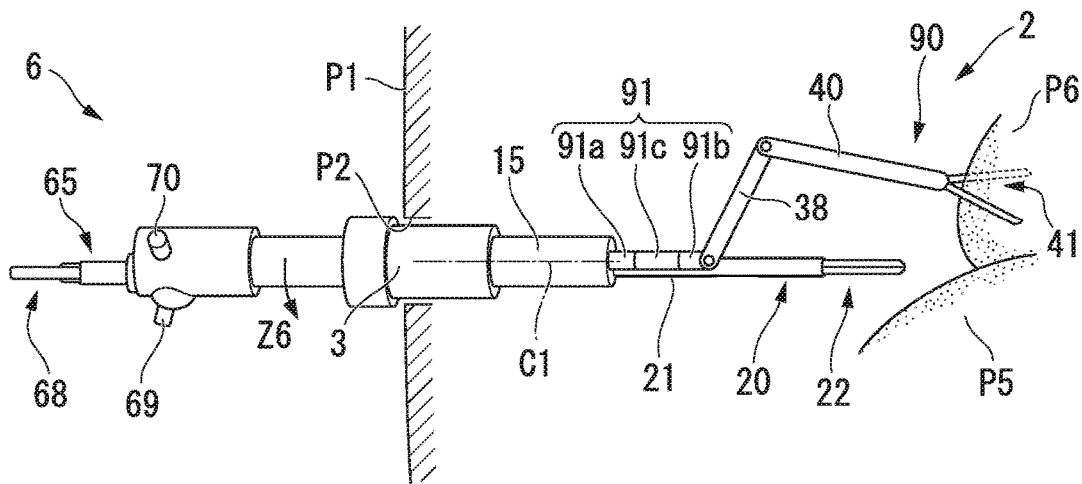
FIG. 24 is a view showing a procedure of treatment using the treatment tool system according to the fourth embodiment of the present invention.

In the treatment tool system 6 configured in this way, even if an operation portion 65 of a treatment tool 2 is rotated around a longitudinal axis C1 of an outer cylindrical tube 15 in a roll direction Z6 as shown in FIG. 24 after an organ P6 is grasped by an assisting portion 41, the link piece 91a is rotated around the longitudinal axis with respect to the link piece 91b so that a distal end side of the treatment assisting portion 90 which grasps the organ P6 cannot be rotated around the longitudinal axis C1.

In other words, when the control mode is a second mode, even if the operation portion 65 is rotated in the roll direction Z6, a position of the assisting portion 41 can be maintained not to move.

The first embodiment to the fourth embodiment of the present invention have been described in detail above with reference to the drawings, but a specific configuration is not limited to the embodiments, and a change, a combination, a deletion, and the like of the configurations are included without departing from the gist of the present invention. In addition, it goes without saying that the configurations shown in the embodiments can be appropriately combined and used.

Figure 25:
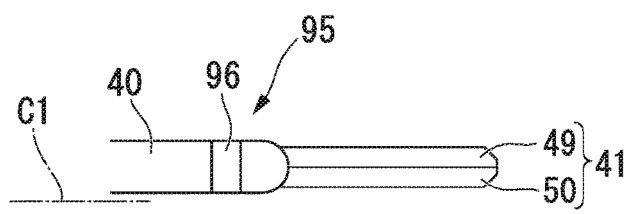
FIG. 25 is a side view of a major part of a treatment tool system of a modified example of the present invention.

For example, in the first embodiment to the fourth embodiment, as shown in FIG. 25, a treatment assisting portion 95 may be provided with a grasping rotary portion 96 which rotates the assisting portion 41 around an axis which is parallel to the longitudinal axis C1 with respect to a distal end of the outer cylindrical tube 15.

The treatment assisting portion 95 is configured as described above so that an orientation of the assisting portion 41 can be changed, and a position as well as the orientation of the assisting portion 41 cannot be moved when the control mode is the second mode.

A distal end surface or the like of the outer cylindrical tube 15 of the treatment tool system has an observing portion by which its outside can be observed so that the treatment tool system may be used as a scope (an endoscope). In this case, treatment can be performed while performing observation using the observing portion and removing an obstacle.

In the treatment portion or the treatment assisting portion, various treatment portions such as a treatment portion which is of the same type and has a different length and an energy treatment portion which uses high frequency energy or the like are detachably prepared for the outer cylindrical tube and may be used for the outer cylindrical tube in a replaceable manner.

In the present embodiment, an amount of movement and an orientation of the outer cylindrical tube 15 of the treatment tool with respect to the trocar 3 are detected by the operation detection portion 55 that is attached to the trocar 3. However, a method of detecting the amount of movement and the orientation of the outer cylindrical tube 15 is not limited thereto. For example, the detection may be performed by a well-known motion sensor which is attached to the outer cylindrical tube 15 or the operation portion 65, and a marker which is attached to the outer cylindrical tube 15 or the operation portion 65 and a three-dimensional motion (an amount of movement and a direction) of the marker may be detected by a well-known motion tracker.

In the present embodiment, the movement instruction portion 69 may be an input portion of a joystick type. However, a configuration of the movement instruction portion is not limited thereto, but a configuration by which amounts of movement of indication directions of two types D and E can be indicated may be used.

The assisting portion 41 may not be provided with the assisting-portion grasping pieces 49 and 50. This is because the organ P6 can be displaced only using the third link 40.

Note that, in the present embodiment, the amount of movement and the orientation of the outer cylindrical tube 15 of the treatment tool with respect to the trocar 3 are detected by the operation detection portion 55 that is attached to the trocar 3. However, a three-dimensional positional information detecting function of the trocar 3 itself is further mounted on the operation detection portion 55, and control can also be performed in consideration of three-dimensional positional information thereof. Thus, since a slight movement of the trocar 3 itself which is derived from displacement, treatment, or the like can also be considered, more precise control is possible.

Although embodiments of the present invention have been described, the technical scope of the present invention is not limited to these embodiments. The combinations of the components in the embodiments can be changed without departing from the gist of the present invention, or each component can be variously modified or removed. The present invention is not limited by the above description.

What is claimed is:

1. A treatment tool system comprising:
a treatment tool comprising:
a cylindrical tube;
an introducing tool configured to be attached to an opening formed in an abdominal wall, the cylindrical tube being inserted in the introducing tool;
a treatment instrument which is disposed at a distal end of the cylindrical tube and used for performing a treatment;
a treatment assisting instrument which is disposed at the distal end of the cylindrical tube and has a grasper configured to assist an operation of the treatment instrument during the treatment, the grasper being capable of moving between a first position near the treatment instrument and a second position moved from the first position in a direction which intersects a longitudinal axis of the cylindrical tube to be spaced a part from the treatment instrument;
a motor configured to move the grasper of the treatment assisting instrument; and
an operating device which is disposed at a proximal end of the cylindrical tube; and
a controller configured to:
receive a detection result from a sensor of the treatment tool, the detection result indicates an amount of movement of the cylindrical tube with respect to the introducing tool and an orientation of the cylindrical tube;
receive an input from an input device of the treatment tool;
operate a first mode to control the motor based on the input received from the input device of the treatment tool,
operate a second mode to control the motor based on the detection result received from the sensor of the treatment tool; and
switch between the first mode and the second mode based on a state of a switch of the treatment tool.

2. The treatment tool system according to claim 1, wherein the controller is configured to operate the second mode to control the motor such that a distance between the treatment instrument and the grasper of the treatment assisting instrument is greater than a predetermined distance.

3. The treatment tool system according to claim 2, wherein the controller is configured to operate the second mode to control the motor such that a position of the grasper of the treatment assisting instrument is not moved.

4. The treatment tool system according to claim 2, wherein the controller controls the motor such that the grasper of the treatment assisting instrument is moved in a direction which is opposite to a direction in which the treatment instrument is moved, when the treatment tool is in the second mode.

5. The treatment tool system according to claim 1, wherein the grasper of the treatment assisting instrument is capable of being moved in a first direction and a second direction which are perpendicular to each other with respect to a proximal end of the treatment assisting instrument.

6. The treatment tool system according to claim 5,
wherein the input device is disposed at the operating device and is capable of being moved in a first indication direction and a second indication direction which are perpendicular to each other with respect to the operating device, and
wherein the controller is configured to, based on the input received from the input device, move the grasper of the treatment assisting instrument in the first direction with respect to the proximal end of the treatment assisting instrument when the input device is moved in the first indication direction with respect to the operating device, and move the grasper of the treatment assisting instrument in the second direction with respect to the proximal end of the treatment assisting instrument when the input device is moved in the second indication direction with respect to the operating device.

7. The treatment tool system according to claim 1, wherein the treatment assisting instrument comprises a plurality of joints which join ends of a plurality of links, and
rotating axes about which the joints rotate the links are parallel to each other.

8. The treatment tool system according to claim 7,
wherein the controller is configured to change angles formed by adjacent links respectively based on the input transmitted from the input device.

9. The treatment tool system according to claim 7, wherein the treatment assisting instrument includes a rotary joint which rotates a distal end side of a proximal end link around a longitudinal axis of the proximal end link which is disposed closest to a proximal end side of the plurality of links, with respect to a proximal end side of the proximal end link.

10. The treatment tool system according to claim 1, wherein the grasper of the treatment assisting instrument is disposed closer to a distal end side than a distal end of the treatment instrument, when the grasper of the treatment assisting instrument is disposed at the first position.

11. The treatment tool system according to claim 1, wherein the grasper of the treatment assisting instrument is a first grasper, and the treatment tool system further comprising:
a treatment operation instrument which operates the treatment instrument,
wherein the treatment instrument includes a second grasper comprising a pair of grasping pieces which are capable of being opened or closed, and
wherein the first grasper of the treatment assisting instrument comprises a pair of assisting-portion grasping pieces which are capable of being opened or closed, and
wherein the treatment operation instrument is configured to open or close the pair of grasping pieces of the second grasper of the treatment instrument.

12. The treatment tool system according to claim 1, wherein the treatment assisting instrument has a rotary which rotates the grasper around an axis which is parallel to the longitudinal axis with respect to the distal end of the cylindrical tube.

13. The treatment tool system of claim 1, wherein:
the sensor is disposed at the introducing tool;
the sensor disposed at the introducing tool is configured to determine a movement amount of the grasper with respect to the introducing tool and an orientation of the grasper corresponding to an orientation of the introducing tool; and the controller is further configured to control the motor to move the grasper based on the determined movement amount of the grasper with respect to the introducing tool and the orientation of the grasper corresponding to an orientation of the introducing tool received from the sensor disposed at the introducing tool.

* * * * *